United States Patent [19]
Ashton et al.

[11] Patent Number: 5,681,964
[45] Date of Patent: Oct. 28, 1997

[54] PERMEABLE, NON-IRRITATING PRODRUGS OF NONSTEROIDAL AND STEROIDAL AGENTS

[75] Inventors: Paul Ashton, Boston; Thomas J. Smith, Weston, both of Mass.; Peter G. Glavinos, Doylestown, Pa.; John D. Conklin, Jr.; Peter A. Crooks, both of Lexington, Ky.; Robert M. Riggs, Birmingham, Ala.; Tadeusz Cynkowski; Grazyna Cynkowska, both of Lexington, Ky.

[73] Assignee: University of Kentucky Research Foundation, Lexington, Ky.

[21] Appl. No.: 318,160

[22] Filed: Oct. 5, 1994

Related U.S. Application Data

[63] Continuation-in-part of Ser. No. 162,388, Dec. 7, 1993, abandoned, which is a continuation of Ser. No. 16,179, Feb. 11, 1993, abandoned, which is a continuation of Ser. No. 601,644, Oct. 23, 1990, abandoned.

[51] Int. Cl.$^6$ .............................. C07D 209/42; C07J 5/00
[52] U.S. Cl. ........................ 548/491; 549/432; 552/582; 560/56; 514/463; 514/573; 514/530
[58] Field of Search .................. 548/491; 549/432; 552/582; 560/53; 574/463, 573, 130

[56] References Cited

U.S. PATENT DOCUMENTS

| | | |
|---|---|---|
| 4,009,283 | 2/1977 | Herr et al. . |
| 4,206,220 | 6/1980 | Sloan . |
| 4,412,994 | 11/1983 | Sloan et al. . |
| 4,439,451 | 3/1984 | Coleman . |
| 4,443,476 | 4/1984 | Lomen . |
| 4,473,584 | 9/1984 | Heckler . |
| 4,477,468 | 10/1984 | Heckler . |
| 4,489,080 | 12/1984 | Lomen . |
| 4,613,505 | 9/1986 | Mizushima et al. . |
| 4,767,751 | 8/1988 | Davis . |
| 4,786,495 | 11/1988 | Bird et al. . |

FOREIGN PATENT DOCUMENTS

| | | |
|---|---|---|
| 1148165 | 6/1983 | Canada . |
| 38 11118C1 | 10/1989 | Germany . |

*Primary Examiner*—Paul J. Killos
*Attorney, Agent, or Firm*—Lowe, Price, LeBlanc & Becker

[57] ABSTRACT

Prodrugs containing an active drug molecule linked to a polyethylene glycol group, and a method of use thereof are described. Exemplary soluble ester prodrugs contain naproxen, triamcinolone acetonide, gancyclovir, taxol, cyclosporin, dideoxyinosine, trihydroxy steroids, and flurbiprofen molecules linked to polyethylene glycol (PEG) groups. Pharmaceutical compositions containing these prodrugs, and a method of using these esters for treating disease states or symptoms are also described.

10 Claims, 6 Drawing Sheets

HYDROLYSIS

PERMEABLE, NON-IRRITATING PRODRUGS OF NONSTEROIDAL AND STEROIDAL AGENTS

This application is a continuation in part application of Ser. No. 08/162,388, filed Dec. 7, 1993 abandoned upon filing this application, which is a continuation of Ser. No. 08/016,179, filed Feb. 11, 1993, now abandoned which is a continuation of Ser. No. 07/601,644, filed Oct. 23, 1990, now abandoned

TECHNICAL FIELD

The present invention relates to non-steroidal or steroidal prodrugs and methods of use thereof. More particularly, the invention relates to soluble ester prodrugs of polyethylene glycol and naproxen, taxol, DDI, gancyclovir, cyclosporin, triamcinolone acetonide, trihydroxy steroid prodrugs, or flurbiprofen prodrugs and a method of using these esters as, for example anti-inflammatory agents, antiviral agents, immunomodulating agents, and for the inhibition of neovascularization, etc., as appropriate.

BACKGROUND ART

Steroidal compounds and non-steroidal compounds are known in the art and their utility is accepted by those of skill in the art and dosage ranges of these compounds are known.

U.S. Pat. No. 4,786,495 to Bird discloses flurbiprofen and salts thereof in admixture with an excipient encompassing fatty acid esters such as polyol esters of polyethylene glycol (see, column 1, line 42+ and claims 1 and 6). The Bird composition contains the drug and an excipient which is separate therefrom. No ester derivatives of the drug are disclosed.

U.S. Pat. No. 4,767,751 to David discloses polyethylene glycol type solubilizers for flurbiprofen (see, column 1, lines 54–65 and column 3, line 36 of Davis). This reference provides a composition comprising two phases, one of which contains a drug. No ester derivatives of the drug is mentioned.

U.S. Pat. No. 4,613,505 to Mizushima discloses esters of flurbiprofen which are different from those of the present invention (see, R in the chemical structure appearing in the abstract and claim 1). The flurbiprofen ester is dissolved in a vegetable oil and emulsified. For human beings the composition may also comprise a nonionic surface active agent such as polyalkylene glycol and copolymers thereof (see, column 4, lines 22–38 of Mizushima).

U.S. Pat. No. 4,489,080 to Lomen discloses alkyl esters of flurbiprofen (see, Example 6 of Lomen). U.S. Pat. No. 4,443,476 to Lomen also relates to alkyl esters of flurbiprofen (see, column 1, lines 34–50 of Lomen). The compounds are disclosed in both patents as being useful for the treatment of adult respiratory distress syndrome and are administered systematically.

U.S. Pat. No. 4,477,468 to Heckler discloses the systemic administration and topical application of flurbiprofen, salts thereof and esters thereof. The esters are ($C_1$-$C_8$) alkyl esters and are prescribed for the prophylactic and therapeutic treatment of herpes type II virus. U.S. Pat. Nos. 4,473,584, 4,443,476 and 4,439,451 are related to U.S. Pat. No. 4,477,468.

U.S. Pat. No. 4,412,994 to Sloan discloses hydroxamic derivatives of flurbiprofen as prodrugs (see, chemical structure appearing in column 2, lines 10–20 and column e, line 32 of Sloan). No esters are disclosed in this patent. U.S. Pat. No. 4,206,220 relates to compounds that are similar to those of U.S. Pat. No. 4,412,994. These compounds are aminoxy derivatives of, e.g., flurbiprofen (see, structure shown in the abstract).

U.S. Pat. No. 4,009,283 to Herr et al discloses alkyl esters of flurbiprofen (see, the chemical structure shown in the abstract). The esters are lower alkyl esters.

Canadian Patent CA 1,148,165 and German Patent DE 3,811,118 disclose esters of flurbiprofen.

It has been recognized in the art that the anti-inflammatory agent, flurbiprofen, produces local irritation when applied for treatment of inflammation. Various techniques have been used to try to lower the dosage of flurbiprofen to the patient, such as techniques for rapid release of the flurbiprofen into the body.

Accordingly, there has been a long standing need in the art for compositions having the effect of flurbiprofen which avoid or reduce the local irritation brought about as compared to flurbiprofen. This is particularly true in the application of the flurbiprofen anti-inflammatory agent to the eye. Surprisingly, certain compounds including prodrugs of polyethylene glycol (PEG) and naproxen, triamcinolone acetonide, or trihydroxy steroid prodrugs, gancyclovir, cyclosporin, taxol, DDI and flurbiprofen prodrugs have now been discovered which show significant therapeutic properties and bioavailability.

SUMMARY OF THE INVENTION

An object of the invention is to provide a prodrug comprising a steroidal or non-steroidal compound linked to a polyethylene glycol of the formula: $HO(CH_2CH_2O)nH$, wherein n=2–12. In a preferred embodiment n=3–6 or 2–6.

Non-steroidal compounds such as indomethacin or naproxen are preferred. Steroidal compounds selected from the group consisting of triamcinolone acetonide, and trihydroxysteroid are also preferred. Other antiviral compounds such as gancyclovir, immunomodulating agents such as cyclosporin, and anti-tumor agents such as taxol, etc., may also be linked to polyethylene glycol to increase their bioavailability.

In an alternative embodiment the steroidal, non-steroidal or other compound is linked to polyethylene glycol by a carbonate link.

A further object of the present invention is to provide a compound having the anti-inflammatory effect of flurbiprofen which either avoids or reduces the local irritation brought about as compared to flurbiprofen. Also provided are other steroidal and non-steroidal prodrugs.

Another object of the present invention is to provide a pharmaceutical composition comprising a compound having the anti-inflammatory effects, for example, of flurbiprofen which avoids or reduces the local irritation brought about as compared to flurbiprofen.

A still further object of the present invention is to provide an improved method for treating inflammation or other disease condition, in a non-human mammal or a human being which comprises the administration of an effective amount of a compound according to the invention or a pharmaceutical composition comprising an effective amount of a compound according to the invention, which has the anti-inflammatory effects or other disease or symptom reducing effects of flurbiprofen or other compound of the invention, to treat disease conditions or symptoms, as appropriate.

Also the invention provides for prodrugs of PEG and naproxen, triamcinolone acetonide, or trihydroxy steroidal drugs. The solubility of flurbiprofen can be decreased and lipophilicity increased, when the molecule is conjugated to two PEG molecules instead of one PEG molecule. The prodrugs of the invention have enhanced transdermal absorption, for example by partitioning into the stratum corneum and remaining there until enzymatically cleaved.

In the alternative the solubility of poorly soluble steroids, such as triamcinolone acetonide can be greatly increased by conjugation to polyethylene glycol (PEG).

Solubility of the steroidal molecules can be adjusted by altering the length of the PEG chain, as can the half-life of the molecule in the body.

DESCRIPTION OF INVENTION

Figure 1:
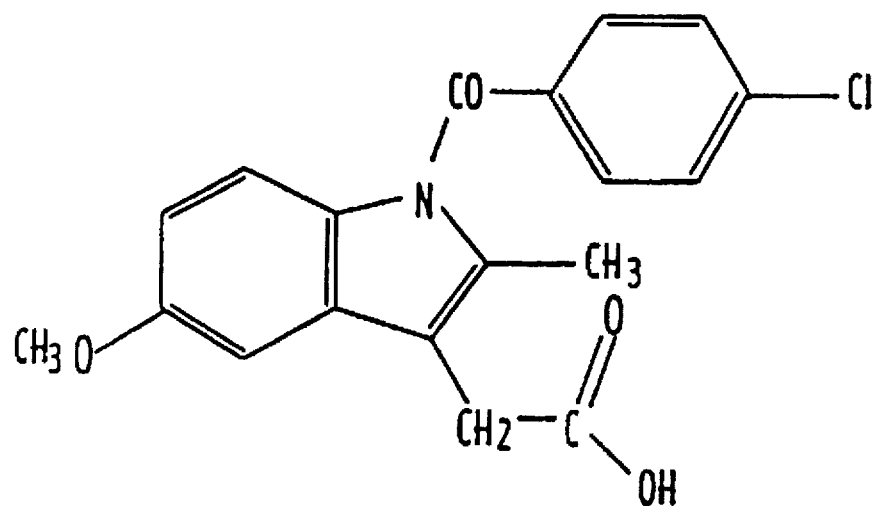
FIG. 1 shows the structure of PEG derivatives of indomethacin.
Figure 1:
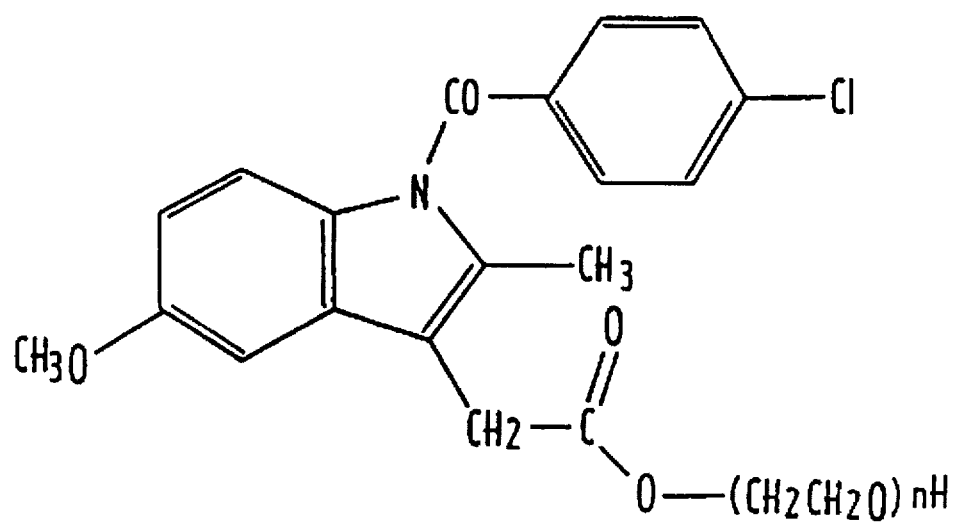
Figure 2:
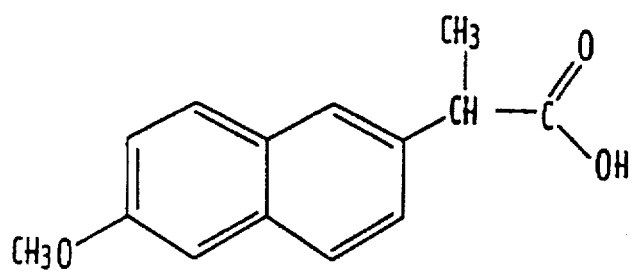
FIG. 2 shows the structure of PEG derivatives of naproxen.
Figure 2:
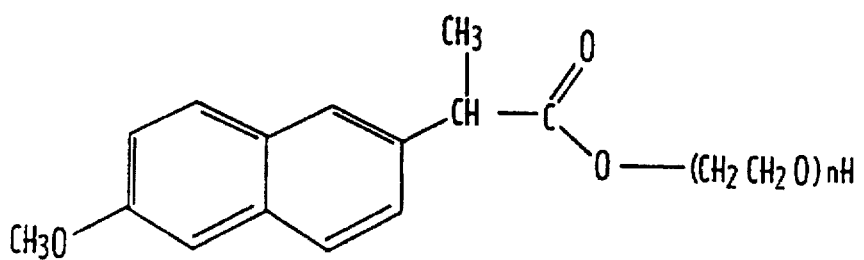
Figure 2:
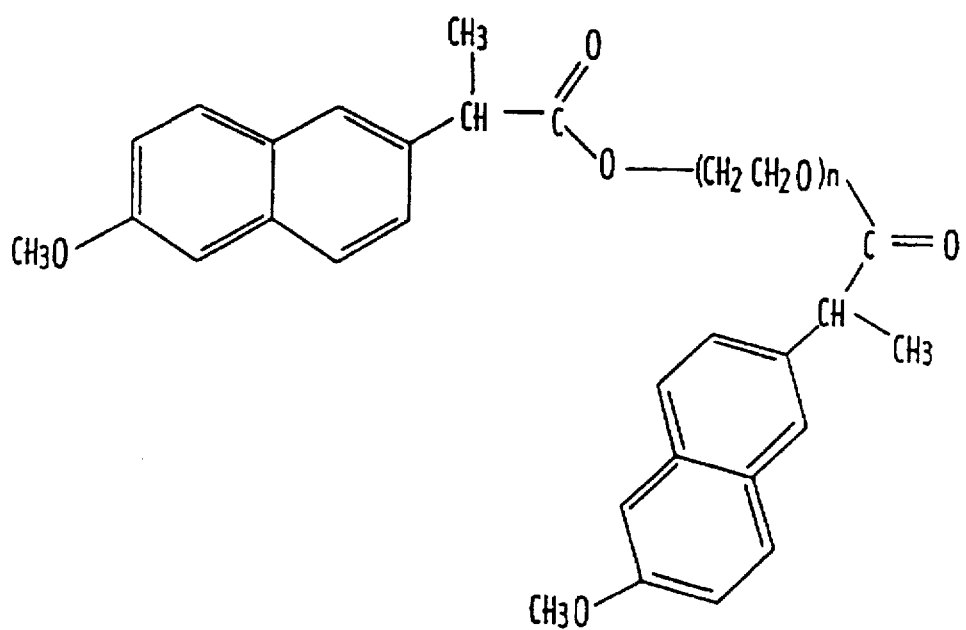
Figure 3:
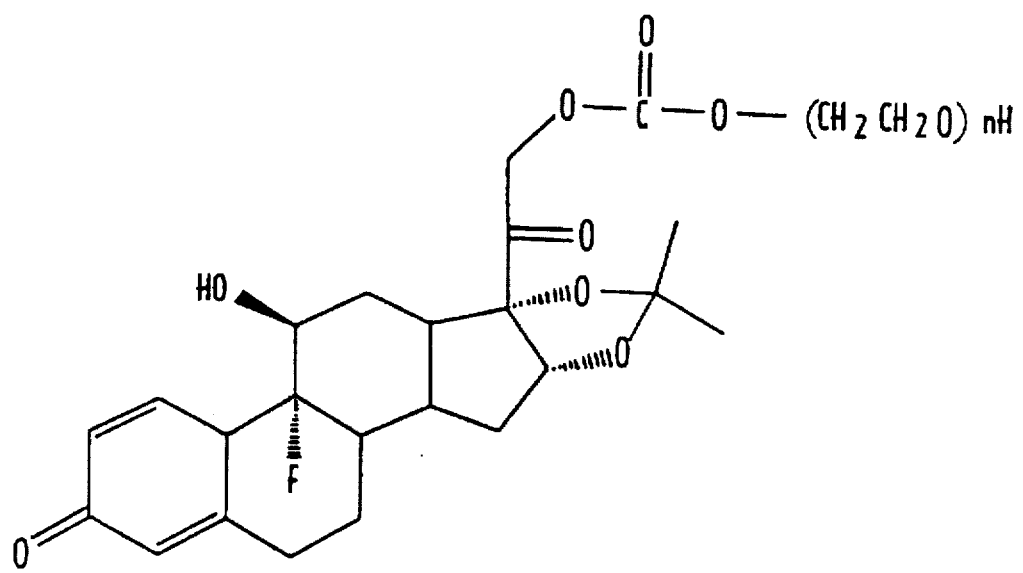
FIG. 3 shows the structure of PEG derivatives of conjugates of triamcinolone acetonide.
Figure 3:
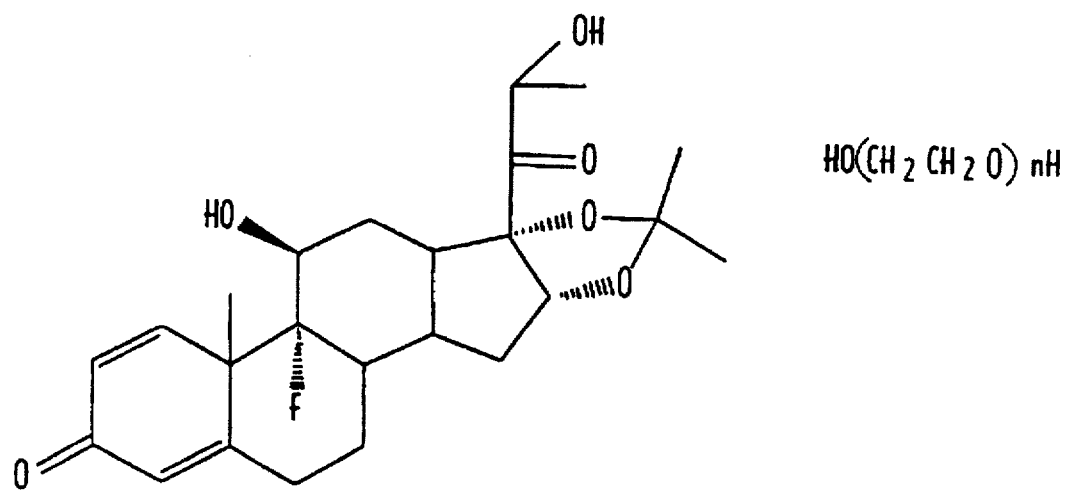
Figure 4A:
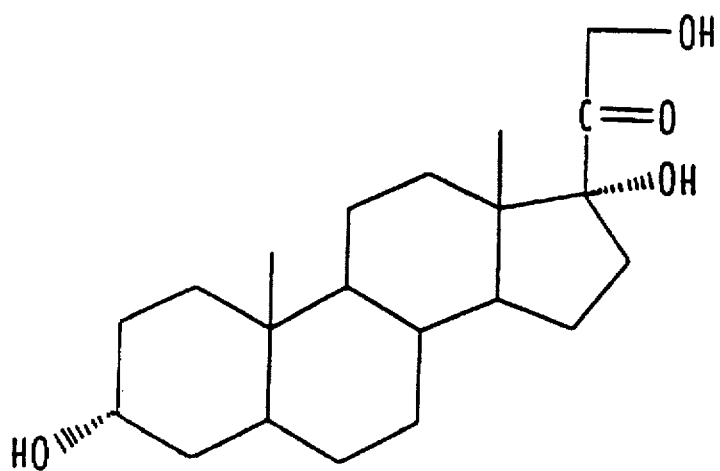
FIGS. 4A–4C show the structure of PEG derivatives of trihydroxysteroid.
Figure 4A:
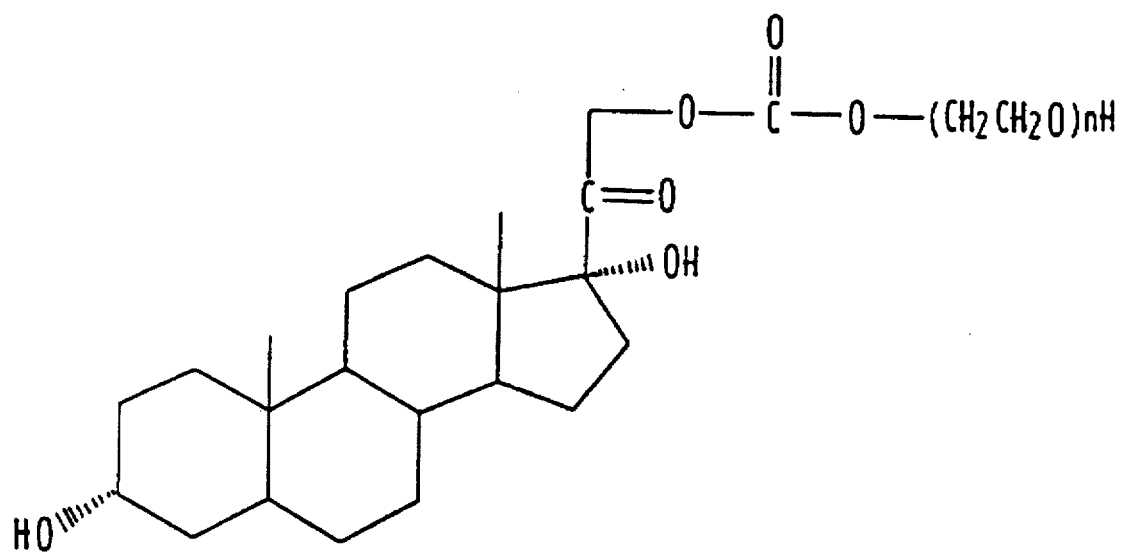
Figure 4B:
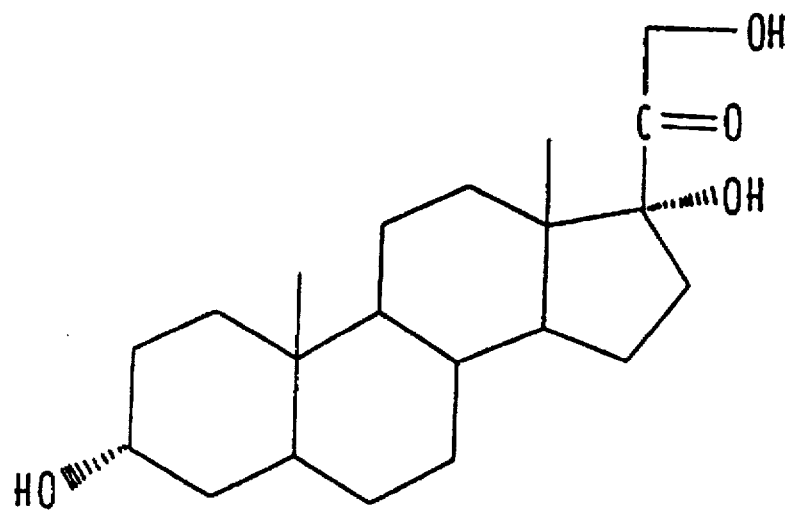
Figure 4B:
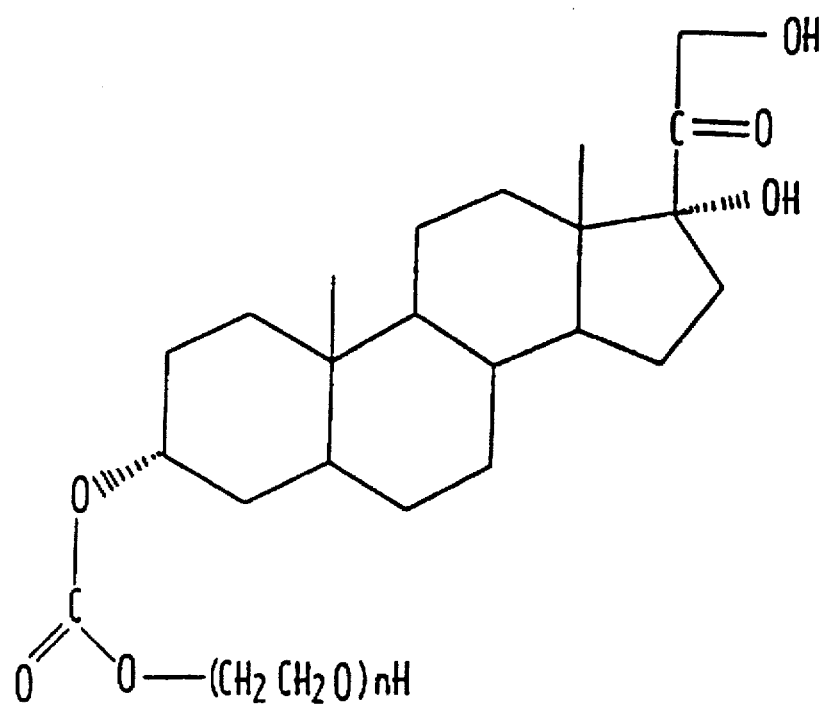
Figure 4C:
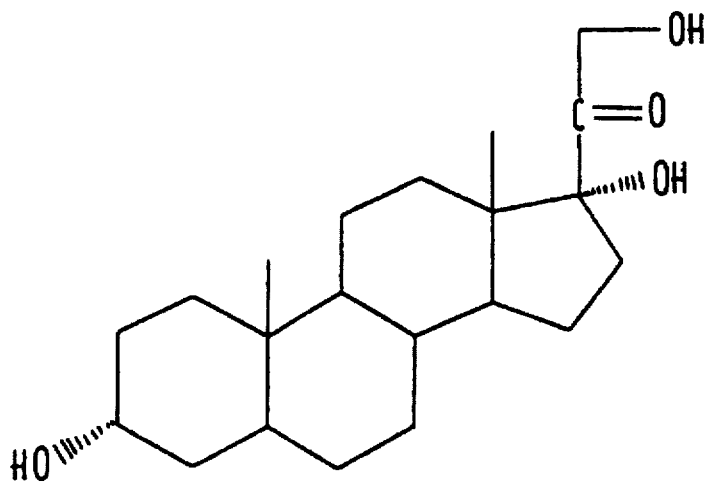
Figure 4C:
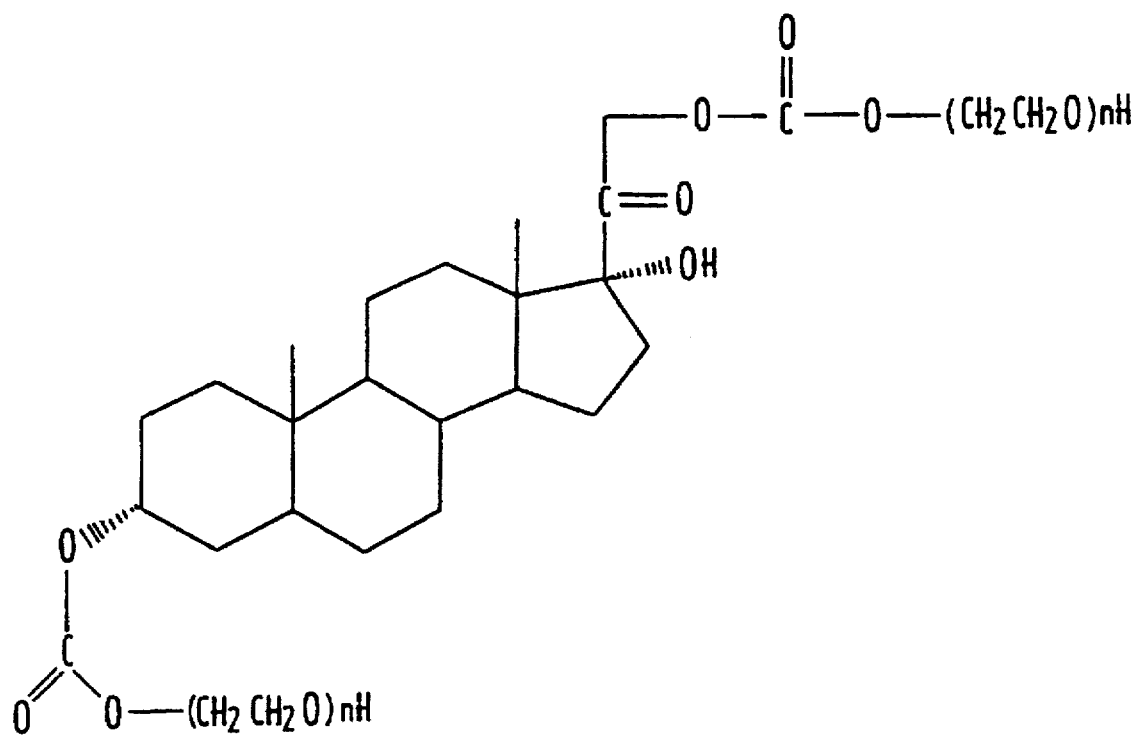

The invention relates to soluble ester prodrugs of polyethylene glycol and naproxen, triamcinolone acetonide, trihydroxysteroid, gancyclovir, cyclosporin, taxol, DDI prodrugs, and flurbiprofen prodrugs. In accordance with this invention there are disclosed compounds of the formula:

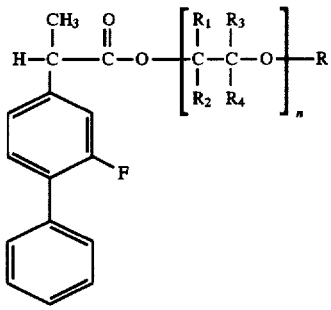

wherein $R_1$, $R_2$, $R_3$ and $R_4$ are selected from the group consisting of H, $C_1$–$C_4$-alkyl and $C_1$–$C_4$-hydroxalkyl and n is a number from 2 to 12, inclusive, and R is selected from the group consisting of H, $C_1$–$C_4$ alkyl, $C_1$–$C_4$ hydroxalkyl and a group having the formula:

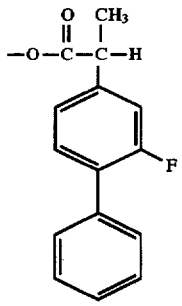

including isomeric forms and pharmaceutically acceptable salts. Pharmaceutically acceptable salts can be, for example, the alkali metal, alkali earth and ammonium salts.

Preferred are compounds according to Formula I wherein $R_1$, $R_2$, $R_3$ and $R_4$ are hydrogen and n is a number from 2–8 and R is H or a group having the formula II. Even more preferred are compounds according to Formula I wherein $R_1$, $R_2$, $R_3$ and $R_4$ are hydrogen and n is 4 or 6 and R is hydrogen or a group having the formula II.

The compounds of Formula I have an asymmetric carbon atom and can exist as optical isomers. For the purpose of this invention, the racemic mixtures and the dextro and levo forms are included within the present invention. The racemic mixtures and the dextro forms are preferred.

Further, the compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of Formula I. The compounds are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the compounds of Formula I can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixers may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydroalcoholic pharmaceutical preparations may be used having an acceptable sweetener such as sugar, saccharine or a biological sweetener and a flavoring agent in the form of an elixir.

Pharmaceutical compositions for parenteral and suppository administration can also be obtained using techniques standard in the art.

A preferred use of the compounds according to the invention is as topical anti-inflammatory agents, as appropriate, suitable for application to either the eyes or the ears. Another preferred use of the compounds is in a transdermal parenteral anti-inflammatory pharmaceutical preparation, which is particularly useful in the treatment of inflamed connective tissue in a mammal such as a human.

Accordingly, compositions suitable for administration to these areas are particularly included within the invention. The above parenteral solutions or suspensions may be administered transdermally and, if desired a more concentrated slow release form may be administered. Accordingly, incorporation of the active compounds in a slow release matrix may be implemented for administering transdermally. The compounds may be administered transdermally at about 1 to 20% of the composition and preferably about 5 to 15% wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy has so far been restricted to a limited number of drugs that possess the desirable physiochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms—Methodology—Drug Delivery*, (Marcel Dekker, New York, N.Y. 1985); and Monkhouse et al, Transdermal drug deliver-problems and promises. *Drug Dev. Ind. Pharm.*, 14, 183–209 (1988).

A penetration enhancer is a chemical compound that, when included in a formulation, temporarily increases the permeability of the skin to a drug allowing more of the drug to be absorbed in a shorter period of time. Several different types of penetration enhancers have been reported such as dimethylsulfoxide, n-decyl methyl sulfoxide, N,N-dimethylacetamide, N,Ni-dimethylformamide, 1-dodecylazacycloheptan-2-one (Azone), propylene glycol, ethanol, pyrrolidones such as N-methyl-2-pyrrrolidone (NMP) and surfactants. See Bronough et al, supra, and Stoughton et al, Azone: a New Non-toxic enhancer of percutaneous penetration. *Drug Dev. Inc. Pharm.*, 9, 725–744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceuticals and is now under consideration for use in products intended for humans. Wells, D. A. et al: Disposition and Metabolism of Double-Labeled [$^3$H and $^{14}$C] N-methyl-2-pyrrolidone in the Rat. *Drug Met. Disps.*, 16, 243–249 (1988). Animal and human experiments have shown very little irritation or sensitization potential. Ames type assays and chronic exposure studies have not revealed any significant toxicity. Wells et al, Mutagenicity and Cytotoxicity of N-methyl-2-pyrrolidone and 4-(methyl amino) Butanoic Acid in the Salmonella/microsome Assay. *J. Appl. Tox.*, 8, 135–139 (1988). N-methylpyrrolidone has also been shown to be an effective penetration enhancer. Barry et al, Optimization and Bioavailability of Topical Steroids: Penetration Enhancers Under Occlusion. *J. Inv. Derm.*, 82, 49–52 (1984); Akter et al, Absorption Through human Skin of Ibuprofen and Flurbiprofen; Effect of Dose Variation, Deposited Drug Films, Occlusion and the Penetration Enhancer N-methyl-2-pyrrolidone. *J. Pharm. Pharmacol.*, 37, 27–37 (1984); Holegaard et al, Vesical Effect on Topical Drug Delivery IV. Effect of N-methylpyrrolidone and Polar Lipids on Percutaneous Transport. *Int. J. Pharm.*, 43, 233–240 (1988); Sugibayashi et al, Effect of Several Penetration Enhancers on the Percutaneous Absorption of Indomethacin in Hairless Rat. *Chem. Pharm. Bull.*, 36, 1519–1529 (1988); Bennett et al, Optimization of Bioavailability of Topical Steroids: Non-occluded penetration Enhancers Under Thermodynamic Control. *J. Pharm. Pharmacol.*, 37, 298–304 (1985); Sasaki et al, Enhancing Effect of Pyrrolidone Derivatives on Transdermal Drug Delivery. 1. *Ing. J. Pharm.*, 44, 14–24 (1988); lee et al, Toxicity of N-methyl-2-pyrrolidone (NMP): Tetratogenic, Subchronic and Two-year Inhalation Studies, *Fund. Appl., Tox.*, 9, 222–235 (1987).

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 10 to 500 mg when administered by either oral or rectal dose from 1 to 3 times daily. This is about 0.2 to about 35 mg per kilogram of the subject's weight administered per day. Preferably about 20 to about 175 mg are administered orally or rectally 1 to 3 times a day for an adult human. The required dose is considerably less when administered parenterally, preferably about 10 to about 60 mg may be administered intramuscularly or transdermally, 1 or 2 times a day for an adult human.

Compounds of the present invention may be administered topically at about 1 to 20 wt % of the composition, and preferably about 5 to 15 wt %.

The reduced cornea damage by polyethylene glycol flurbiprofenate and bis-flurbiprofenate prodrugs in albino rabbit eyes was assessed by differential scanning calorimetry. Tests were conducted to investigate the effects of flurbiprofen and the polyethylene glycol flurbiprofen ester and the diester prodrugs on the cornea epithelium. The tests demonstrate that surprisingly, the soluble ester prodrugs reduce the local irritation which is observed in the treatment of flurbiprofen which is not esterified, that is flurbiprofen which is in the free acid form. The effects of these drugs on the molecular structure of the cornea epithelium were assessed by differential scanning calorimetry. Fresh enucleated albino rabbit eyes were treated in solutions and also in suspensions of flurbiprofen and also in solutions and suspensions of the polyethylene glycol esters and diesters of flurbiprofen in isotonic glutathione buffered ringer solution for 10 minutes. The cornea epithelium was then scraped from the corneas and immediately analyzed by differential scanning calorimetry over the range of 40°–110° C.

Whenever a normal rabbit's cornea epithelium was analyzed a large endothermic transition at 64°±2° C. was observed. It has been established by previous work that this particular peak which was observed was due to a lipid\protein phase transition. It can be readily demonstrated that compounds which are known to damage the cornea, for example benzalkonium chloride greatly reduce the intensity of this observed peak.

When the albino rabbit eyes were treated with a saturated solution of flurbiprofen the cornea epithelium showed no phase transitions which indicates a substantially total breakdown of the normal protein/lipid structure. A reduced phase transition was found in corneas which had been treated with a 0.025% flurbiprofen. Observing this data is consistent with reports that flurbiprofen impairs cornea barrier function in vitro and is found to be irritating in man.

Surprisingly, the cornea epithelium which is taken from albino rabbit eyes which have been treated with a saturated solution of the polyethylene glycol bis-flurbiprofenate showed only a marginal decrease in the exothermic transition when assessed by the differential scanning calorimetry.

Accordingly, this suggests a significant reduction in the topical toxicity of the prodrugs according to the invention as compared to the flurbiprofen. Additional tests, to assess the irritancy of the polyethylene glycol flurbiprofenate and polyethylene glycol bis-flurbiprofenate, confirm that there is a significant reduction of the irritancy of the prodrugs according to the invention as compared to the flurbiprofen acid form.

Tests were conducted to determine that the polyethylene glycol flurbiprofenates were prodrugs, that during transport across the cornea the polyethylene flurbiprofenates are substantially converted to flurbiprofen.

Prepared was a 5% solution of an ester according to the present invention in glucathione buffered ringers solution, (approximately equivalent to a 1–3% flurbiprofen solution). Human corneas were prepared and the experiment was run for 210 minutes. After 210 minutes the corneas remained clear, indicating a low degree of irritability. Little prodrug penetrated the receptor side, nearly all was converted to the flurbiprofen acid form during transport. This experiment was repeated using albino rabbit corneas mounted chambers. Samples were taken every 30 minutes for 210 minutes which were assayed by HPLC (high pressured liquid chromatography). The corneas appeared clear, hydration was determined to be about 80%. Even though the permeation was rapid no ester was found on the receptor side since the flurbiprofen acid form was produced during transport.

Another experiment was performed with tetraethylene glycol flurbiprofenate and tetraethylene glycol bis-flurbiprofenate to determine the irritancy of these prodrugs in the rabbit eye.

25 microliters of tetraethylene flurbiprofenate were dropped into each eye of two rabbits each day for seven days. Also, 30 microliters of tetraethylene glycol bis-flurbiprofenate was dropped into each eye of two rabbits each day for 7 days. A control using 25 microliters of flurbiprofen was dropped into each eye of two rabbits for seven days. Each morning the rabbit's eyes were examined by slit lamp for evidence of cornea damage and irritation. After seven days the animals were sacrificed and samples of the aqueous humor and vitreous humor were obtained for analysis of flurbiprofen and a flurbiprofen ester. The eyes were also examined by electron microscopy. The flurbiprofenates were converted into the flurbiprofen acid form during transport into the eye. The degree of irritation to the cornea was significantly reduced by use of the prodrug as compared to flurbiprofen in the acid form. The test was repeated using 10 microliters of each of the substances each day for seven days with similar results.

Accordingly, these compounds are potent antiinflammatory agents. By maintaining the activity of the flurbiprofen and having a low degree of irritation to the subject when administered, significant advancements in the art of treating inflammation have been accomplished. Such surprising results were not expected.

The compounds of the invention can be prepared by conventional acid catalyzed or base catalyzed esterification procedures known to the art. For example, the flurbiprofen acid form can be reacted with the alcohol in the presence of an acid or base esterification catalyst to produce the final product esters according to the present invention.

The following specific examples of this invention are not intended to limit the invention disclosed. Based upon the above disclosure and the following examples, other variations and permutations on the present invention will be apparent to one of ordinary skill in the art.

Preparation of Compound according to Formula I.

EXAMPLE 1

Tetraethylene glycol 2-(-Fluoro-4 biphenylyl)propionate and Tetraethylene glycol bis-2-(2-fluoro-4-biphenylyl) propionate.

A mixture of 4 grams (0.0041 moles) of flurbiprofen (2(2-fluoro-4-biphenylyl)propionic acid) and 30 ml of $PEG_{200}$ (polyethylene glycol, i.e. tetraethylene glycol) (0.169 moles) and 4.2 ml of $BF_3$-etherate (0.0328 moles) were refluxed for 48 hours in 180 ml of acetonitrile. TLC (thin layer chromatography) indicated that the reaction had essentially reached completion in 12 hours. Following in vacuo removal of acetonitrile, a yellow-gold oily solution resulted. A sample of this product was subjected to TLC analysis on 60 angstroms silica gel plates 250 micrometers thick with F254 indicator; using ethyl acetate as the eluting solvent. Following development, the plates were dried under hot air and then read using a 254 nanometer UV lamp and iodine vapor. Compounds having flurbiprofen derivatives show up under the ultraviolet light while PEG200 derivatives show up on the presence of iodine vapor as a yellow spot. The impurities and excess $PEG_{200}$ with separated from the product to yield spots on the plate which are both UV and iodine vapor active thereby indicating that the esterification reaction has been successful. The remaining product was then separated from the excess tetraethylene glycol by eluting the solution down a 4 centimeter×60 centimeter glass column packed with 60 angstrom silica gel/ethyl acetate slurry. About 4 grams of product (greenish oil) was obtained by the first elution (the flow rate of eluant (ethyl acetate) was about 5 ml per minute). A second elution was performed to resolve the flurbiprofen ester from the impurities and to separate the monoester from the diester by the difference in flow rate. The monoester was eluted as the fourth fraction in the second elution. Yielded was about 1 gram of tetraethylene glycol 2-(2-fluoro-4-biphenylyl)propionate of product and about 1.5 grams of tetraethylene glycol bis-2-(2-fluoro-4-biphenylyl)propionate of product. The structures were characterized by infrared spectra which confirm the structures.

| Signal (amt) | Assessment |
|---|---|
| IR Data of Tetraethylene Glycol Flurbiprofenate (Monoester) | |
| 3460 (broad | —OH |
| 3020, 3060 (weak) | aromatic C—H |
| 2940, 2860 (broad) | aliphatic C—H |
| 1730 (strong) | C=O (ester) |
| 1620 (weak) | C=C (aromatic) |
| 1240 (broad | C—O (ester) |
| 1120 | C—O (ester) |
| IR Data of Tetraethylene Glycol bis-Flurbiprofenate (Diester) | |
| 3020, 3060 (weak) | aromatic C—H |
| 2940, 2860 (broad) | aliphatic C—H |
| 1730 (strong) | C=O (ester) |
| 1620 (weak) | C=C (aromatic) |
| 1240 (broad | C—C (ester) |
| 1120 | C—O (ester) |

EXAMPLE 2

Hexaethylene Glycol Fluriprofenate

To 1 g (0.0041 moles) flurbiprofen and 20 mL (0.07 moles) PEG300 (hexaethylene glycol) in 150 mL of ACN were added 1.01 mlles $BF_3$ etherate (as catalyst). This solution was refluxed for about 25 hours. The solvent was removed in vacuo. The product was purified in a manner similar to the purification of the esters of Example 1, above. Yielded were about ⅓ gram of hexaethylene glycol flurbiprofenate and about ⅕ hexaethylene glycol bis-flurbiprofenate.

| Signal (amt) | Assessment |
|---|---|
| IR Data of Tetraethylene Glycol Flurbiprofenate (Monoester) | |
| 3460 (broad) | —OH |
| 3020, 3060 (weak) | aromatic C—H |
| 2940, 2860 (broad) | aliphatic C—H |
| 1730 (strong) | C=O (ester) |
| 1620 (weak) | C=C (aromatic) |
| 1240 (broad) | C—O (ester) |
| 1120 | C—O (ester) |
| IR Data of Hexaethylene Glycol bis-Flurbiprofenate (Diester) | |
| 3020, 3060 (weak) | aromatic C—H |
| 2940, 2860 (broad) | aliphatic C—H |
| 1730 (strong) | C=O (ester) |
| 1620 (weak) | C=C (aromatic) |
| 1240 (broad) | C—O (ester) |
| 1120 | C—O (ester) |

EXAMPLE 3

Octaethylene glycol flurbiprofenate and octaethylene glycol bis-flurbiprofenate

To one gram of flurbiprofen and about 30 mL of $PEG_{400}$ (octaethylene glycol) in 150 mL of ACN were added to 1.01 mL of $BF_3$-etherage (as catalyst). This solution was refluxed for about 12 hours. The work up was substantially as indicated in Example 1 above. Yielded was about ½ gram of octaethylene glycol flurbiprofenate. The structure was confirmed by IR data.

EXAMPLE 4

NMR spectra were recorded on a Varian VXR-300 spectrometer. Chemical shifts are in ppm relative to internal tetramethylsilane. Column chromatography was performed using Aldrich silica gel (200–400 mesh). All compounds showed satisfactory purity by TLC on Analtech silica gel GF plates.

Prodrugs from the Reaction of Naproxen Acid Chloride with Polyethylene Glycols (PEG), $HO(CH_2CH_2O)nH$, n=2, 3, 4, 6.

Esters of naproxen and various polyethylene glycols have been synthesized as shown in Scheme 1. The following procedure allows one to obtain and easily separate two prodrugs from one reaction.

To a solution of an appropriate polyethylene glycol (1 mmol) in anhydrous dichloromethane (10 mL) was added pyridine (1.4 eq.) and naproxen acid chloride (1 mmol). The mixture was stirred overnight at room temperature, then washed successively with a saturated solution of sodium bicarbonate, water and brine. The organic phase was dried over $Na_2SO_4$, evaporated to an oil and the reaction products separated as shown below:

Compounds 1a and 2a; Naproxen synthesis:

The residue was chromatographed initially with benzene acetone (20:1) up to benzene:acetone (9.1) to give first the less polar diester of naproxen and diethylene glycol 2a (97 mg, 18.3% ), and then monoester 1a (178 mg, 56%) as oils. 2a $^1$H NMR ($CDCL_3$) β 1.55 (d, 6H, $CHCH_3$), 3.44 (m, 4H, $OCH_2$), 3.82 (q,2H,$CHCH_3$), 3.85 (s, 6H, $OCH_3$), 4.09 (m, 4H, $COOCH_2$), 7.02–7.71 (m, 12H, aromatic) ppm; $^{13}$C NMR ($CDCL_3$) β 174.48 (C=O), 157.60 (C-6), 135.51 (C-2), 133.64 (C-10), 129.20 (C-8), 128.84 (C-9), 129.09 (C-4), 126.18 (C-3), 125.95 (C-1), 118.96 (C-7), 105.52 (C-5), 68.87 ($COOCH_2$), 63.82 ($OCH_2$), 55.22($OCH_3$), 45.27 ($CHCH_3$), 18.48 ($CHCH_3$) ppm. 1a $^1$H NMR ($CDCL_3$) β 1.58 (d, 3H, $CHCH_3$), 3.40 (m, 2H, $CH_2OH$), 3.55(m, 2H, $OCH_2$), 3.85 (q, 1H $CHCH_3$), 3.86 (s, 3H, $OCH_3$), 4.21 (m, 2H, $COOCH_2$, 7.06–7.72 (m, 6H, aromatic) ppm; $^{13}$CNMR ($CDCL_3$) β 174.48 (C=O), 157.41 (C-6), 135.31 (C-2), 133.47 (C-10), 129.03 (C-8), 128.67 (C-9), 126.93 (C-4), 125.99 (C-3), 125.77 (C-1), 118.82 (C-7), 105.33 (C-5), 72.13 ($COOCH_2$), 68.72, 63.66, 61.34 (3x$OCH_2$), 55.05 ($OCH_3$), 45.13 ($CHCH_3$), 18.29 ($CHCH_3$) ppm.

Compounds 1b and 2b; Naproxen synthesis

The crude oil (284 mg) was separated by chromatography. The column bed was washed with initially benzene:acetone (15:1) up to benzene:acetone (9:1). Two fractions were collected: the diester of naproxen and trimethylene glycol 2b (112 mg, 19.5% yield) and monoester 1b (173 mg, 47.5% yield) as colorless oils. 2b $^1$H NMR ($CDCL_3$) β 1.60 (d, 6H, $CHCH_3$), 3.35 (s, 4H, $OCH_2CHO_2O$), 3.55 (t, 4H, $OCH_2$), 3.88 ($q_2$2H, $CHCH_3$), 3.88 (s, 6H, $OCH_3$), 4.02 (m, 4H, $COOCH_2$), 7.12–7.71 (m, 12H, aromatic) ppm; $^3$CNMR ($CDCL_3$) β 174.47 (C=O), 157.50(C-6), 135.50 (C-2), 133.55 (C-10), 129.14 (C-8), 128.77 (C-9), 126.99 (C-4), 126.14 (C-3), 125.87 (C-1), 118.88 (C-7), 105.41 (C-5), 70.26 ($COOCH_2$), 68.84 ($OCH_2$), 63.80 ($OCH_2$), 55.15 ($OCH_3$), 45.21 ($CHCH_3$), 18.45 ($CHCH_3$) ppm. 1b $^1$H NMR ($CDCL_3$) β 1.58 ($d_2$ 3H, $CHCH_3$), 2.62 (1H, OH), 3.41–3.72 (m, 8H,$CH_2O$), 3.90 (q, 1H, $CHCH_3$), 3.91 (s, 3H, $OCH_3$), 4.22 (m, 2H, $COOCH_2$), 7.06–7.72 (m, 6H, aromatic) ppm; $^{13}$C NMR ($CDCL_3$) β 174.57 (C=O), 157.55 (C-6), 135.54 (C-2), 133.62 (C-10), 129.20 (C-8), 128.84 (C-9), 127.05 (C-4), 126.21 (C-3), 125.95 (C-1), 118.92 (C-7), 105.48 (C-5), 72.36 ($COOCH_2$), 70.43, 70.16, 68.96, 63.83, 61.62 (5x$OCH_2$), 55.23 ($OCH_3$), 45.25 ($CHCH_3$), 18.45 (CH $CH_3$) ppm.

Compounds 1c and 2c; Naproxen Synthesis.

The oily residue (294 mg) was chromatographed using initially benzene:acetone (12:1) up to benzene:acetone (4:1)

as a solvent system. Two products were isolated: the diester of naproxen and tetraethylene glycol 2c (170 mg, 27.5% yield) and monoester 1c (150 mg, 37% yield). (2c) $^1$H NMR (CDCL$_3$) β 1.55 (d, 6H, CHC$\underline{H}_3$), 7.07–7.72 (m, 12H, aromatic) ppm; $^1$C NMR (CDCL$_3$) β 174.52 (C=O), 157.54 (C-6), 135.54(C-2), 133.59 (C-10), 129.18 (C-8), 128.81 (C-9), 127.02 (C-4), 126.18 (C-3), 125.89 (C-1), 118.88 (C-7), 105.46 (C-5), 70.38, 70.36, 68.92, 63.87 (4×OCH2), 55.20 (OCH$_3$), 45.25 ($\underline{C}$HCH$_3$), 18.49 (CH$\underline{C}$H$_3$) ppm. (1c) $^1$H NMR (CDCL$_3$) β 1.58 (d, 3H, CHC$\underline{H}_3$), 2.75 (1H, OH), 3.51–3.73 (m, 14H, CH$_2$O), 3.88 (q, 1H, C$\underline{H}$CH$_3$), 3.90 (s, 3H, OCH$_3$), 4.22 (m, 2H, COOCH$_2$), 7.08–7.72 (m, 6H, aromatic) ppm; $^{13}$C NMR (CDCL$_3$ β 174.41 (C=O), 157.45 (C-6), 135.46(C-2), 133.51 (C-10), 129.09 (C-8), 128.75 (C-9), 126.93 (C-4), 126.10 (C-3), 125.81 (C-1), 118.79 (C-7), 105.39 (C-5), 72.32 (COO$\underline{C}$H$_2$), 70.37, 70.31, 70.27, 70.11, 68.85, 63.80, 61.51 (7×OCH$_2$), 55.11 (OCH$_3$), 45.17 ($\underline{C}$HCH$_3$), 18.37 (CH$\underline{C}$H$_3$) ppm.

Compounds 1d and 2d; Naproxen Synthesis

The crude oil ( 337 mg ) was separated by chromatography. The column bed was washed with initially benzene:acetone (9:1) up to benzene:acetone (2:1) to give first the less polar diester of naproxen and hexaethylene glycol 2d (100 mg, 14.2% yield) and then the monoester 1d (230 mg, 46.7% yield) as oils. 2d $^1$H NMR (CDCL$_3$) β 1.57 (d, 6H, CHC$\underline{H}_3$), 3.48, 3.55 (2s, 16H, OCH$_2$), 3.60 (t, 4H, OCH$_2$), 7.07–7.72 (m, 12H, aromatic) ppm; $^{13}$CNMR (CDCL$_3$) β 174.38 (C=O), 157.40 (C-6), 135.40 (C-2), 133.46 (C-10), 129.05 (C-8), 128.70 (C-9), 126.89 (C-4), 126.06 (C-3), 125.77 (C-1), 118.75 (C-7), 105.34 (C-5), 70.30, 70.29, 70.28, 70.26, 68.80, 63.76 (12×OCH$_2$), 55.08 (OCH$_3$), 45.11 ($\underline{C}$HCH$_3$), 18.35 (CHC$\underline{H}_3$) ppm. 1d HNMR (CDCL$_3$) β 1.58 (d, 3H, CHC$\underline{H}_3$), 3.00 (s, 1H, OH), 3.46–3.75 (m, 22H, CH$_2$O), 3.85 (q, 1H, C$\underline{H}$CH$_3$), 3.88 (s, 3H, OCH$_3$), 4.22 (m, 2H, COOCH$_2$), 7.08–7.73 (m, 6H, aromatic) ppm; $^{13}$CNMR β 174.41 (C=O, 157.42 (C-6), 135.43 (C-2), 133.48 (C-10), 129.07 (C-8), 128.70 (C-9), 126.91 (C-4), 126.08 (C-3), 125.78 (C-1), 118.76 (C-7), 105.35 (C-5), 72.40 (COO$\underline{C}$H$_2$), 70.38, 70.32, 70.28, 70.06, 68.80, 63.79, 61.45 (11×OCH$_2$), 55.09 (OCH$_3$), 45.12 ($\underline{C}$HCH$_3$), 18.36 (CH$\underline{C}$H$_3$) ppm.

Reaction of Naproxen Acid Chloride with Monoprotected Tetraethylene Glycol

An alternative approach for the preparation of the naproxen-polyethylene glycol prodrugs is also shown in Scheme 1 below. This method required the selective protection of one of the two PEG-hydroxyl groups as a silyl derivative. Subsequent acylation and deprotection led to the expected prodrug, according to the description below.

To a solution of mono(τ-butyldiphenylsilyl) tetraethylene glycol (1 mmol) in 10 mL of dry dichloromethane and 113 μL of pyridine at 0° C. was added naproxen acid chloride (1.1mmol). The resulting mixture was then stirred at room temperature overnight, washed successively with sodium bicarbonate solution, water, brine and finally dried over Na$_2$SO$_4$. The crude product was purified by chromatography (hexane:ethyl acetate, 3:1) to yield 620 mg (96.5%) of the monoprotected pure ester of naproxen and tetraethylene glycol 3. $^1$H NMR (CDCL$_3$) β 1.05 (s, 9H, τ-Bu), 1.58 (d, 3H, CHC$\underline{H}_3$), 3.51–3.81 (m, 14H, OCH$_3$), 3.85 (q, 1H, C$\underline{H}$CH$_3$), 3.87 (s, 3H, OCH$_3$), 4.20 (m, 2H, COOCH$_3$), 7.07–7.72 (m, 6H, aromatic) ppm.

Deprotection of Compound 3 (Scheme 1 below).

To a solution of 620 mg of 3 in THF (10 mL) at 0° C. was added glacial acetic acid (0.3 mL) and a 1M solution of tetrabutylammonium fluoride in THF (2.5 mL). The reaction mixture was stirred at room temperature overnight, diluted with diethyl ether (20 mL) and washed successively with ammonium chloride solution, water, and brine. Drying over Na$_2$SO$_4$ and solvent evaporation afforded a colorless oil, which was purified by column chromatography (benzene:acetone, (4:1). The monoester of naproxen and tetraethylene glycol 1c was obtained as a colorless oil (360 mg, 92.3% yield).

Reaction of Flurbiprofen Acid Chloride with Monoprotected Trimethylene Glycol (Scheme 2 below)

Flurbiprofen acid chloride (434 mg, 1.65 mmol) was added to a solution of mono(τ-butyldiphenylsilyl)-trimethylene glycol (1.5 mmol) and 170 μL of pyridine in 15 mL of dry dichloromethane at 0° C. The resulting mixture was then stirred at room temperature overnight washed successively with sodium bicarbonate solution, water, brine and finally dried over Na$_2$SO$_4$. The residue was purified by column chromatography (hexane:ethyl acetate, 6:1 up to 4:1) yielding 774 mg (82%) of pure 4. $^1$H NMR(CDCL$_3$) β 1.03 (s, 9H, τ-Bu), 1.52 (d, 3H, CH$_3$), 3.51–3.73 (m, 10H, OCH$_2$), 3.82 (q, 1H, C$\underline{H}$CH$_3$), 4.25 (m, 2H, COOCH$_2$), 7.11–7.70 (m, 8H, aromatic ppm).

Deprotection of Compound 4.

A 1M solution of tetrabutylammonium fluoride in THF (3.1 mL) was added to an ice-cooled solution of 4 (774 mg, 1.26 mmol) and glacial acetic acid (380 μL) in 10 mL of THF. After the mixture was stirred at room temperature overnight, diethyl ether (20 mL) was added and the solution washed with ammonium chloride solution, water and brine. The crude product was purified by column chromatography (benzene:acetone, 9:1, up to 4:1) yielding 391 mg (82.4%) of the pure ester of flurbiprofen and trimethylene glycol 5. $^1$H NMR (CDCL$_3$) β 1.55 (d 3H, CH$_3$), 2.40 (1H, OH), 3.55–3.75 (m 10H$_{13}$, OCH$_2$), 3.80 (q, 1H, C$\underline{H}$CH$_3$), 4.27 (m, 2H, COOCH$_2$), 7.1–7.55 (m, 8H, aromatic) ppm: $^{13}$C NMR (CDCL$_3$) β 173.94 (C=O), 159.50 (d,J=248 Hz, C-2), 141.65 (C-1), 135.41 (C-4), 128.85 (C-6), 128.80, 128.41, 127.62 (C-2',3',4'), 128.80 (C-1'), 123.55 (C-5), 116.21 (C-3), 72.46, 70.55, 70.31, 69.09, 64.07, 61.75 (6×CH$_2$), 44.81 ($\underline{C}$HCH$_3$), 18.52 (CH$_3$) ppm.

Prodrugs From the Reaction of Flurbiprofen Acid Chloride with Polyethylene Glycols (PEG), HO(CH$_2$, CH$_2$O$_n$, n=4, 6 (Scheme 2).

To a solution of the appropriate polyethylene glycol (0.83 mmol) in 10 mL of dry dichloromethane was added at room temperature 94 μL of pyridine followed by 221.9 mg (0.83 mmol) of flurbiprofen acid chloride. The reaction mixture was stirred at room temperature overnight, washed successively with sodium bicarbonate solution, water, brine and finally dried over Na$_2$SO$_4$. In this one reaction, two prodrugs were obtained, which were easily separated as described below.

Compounds 6a and 7a; Flurbiprofen

The crude mixture (238 mg) was separated by chromatography. The column bed was washed with benzene:acetone (9:1) up to benzene:acetone (4:1). Two fractions were collected: first the diester of flurbiprofen and tetraethylene glycol 7a (119 mg, 22% yield) followed by monoester 6a (105 mg, 30% yield), both as colorless oils. 7a $^1$H NMR (CDCL$_3$) β 1.55 (d, 6H, CH$_3$), 3.52–3.73 (m, 12H, OCH$_2$), 3.78 (q, 2H, C$\underline{H}$CH$_3$, 4.25 (m, 4H, COOCH$_2$), 7.11–7.63 (m, 16H, aromatic) ppm; $^{13}$C NMR (CDCL$_3$) β 173.78 (C=O), 159.51 (d, J=248 Hz, C-2), 141.69 (C-1), 135.36 (C-4), 130.64 (C-6), 128.81, 128.35, 127.57 (C-2', 3', 4'), 127.75 (C-1'), 123.52 (C-5), 115.2 (C-3), 70.48, 70.44, 68.90, 63.99 (8×CH$_2$), 44.83 ($\underline{C}$HCH$_3$), 18.31 (CH$_3$) ppm. 6a $^1$H NMR (CDCL$_3$) β 1.55 (d, 3H, CH$_3$), 2.75 (1H, OH), 3.55–3.75 (m, 14H, OCH$_2$), 3.81 (q, 1H, C$\underline{H}$CH$_3$), 4.25 (m, 2H, COOCH$_2$), 7.10–7.55 (m, 8H, aromatic) ppm; $^{13}$C NMR (CDCL$_3$) β 173.78 (C=O), 159.50 (d, J=248 Hz, C-2), 141.65 (C-1), 135.31 (C-4), 130.59 (C-6), 128.76, 128.30, 127.52 (C-2', 3', 4'), 127.70 (C-1'), 123.47 (C-5), 115.13 (C-3), 72.36, 70.46, 70.37, 70.36, 70.15, 68.88, 63.96, 61.54 (8×CH$_2$), 44.52 (CHCH$_3$), 18.13 (CHCH$_3$) ppm.

Compounds 6b and 7b; Flurbiprofen

The crude oil (337 mg) was chromatographed with benzene:acetone (9:1) up to benzene:acetone (4:1). Two products were isolated; the diester of flurbiprofen and hexaethylene glycol 7b (155 mg, 25.3% yield) and monoester 6b (163 mg, 38.5% yield) as colorless oils. 7b $^1$H NMR (CDCL$_3$) β 1.54 (d, 6H, CH$_3$), 3.51–3.72 (m, 20H, OCH$_2$), 3.78 (q, 2H, CHCH$_3$), 4.25 (m, 4H, COOCH$_2$), 7.12–7.52 (m, 16H, aromatic) ppm; $^{13}$C NMR (CDCL$_3$) β 173.84 (C=O), 159.50 (d, J=248 Hz, C-2), 141.71 (C-1), 135.40 (C-4), 130.68 (C-6), 128.84, 128.37, 127.59 (C-2',3',4'), 127.78 (C-1'), 123.52 (C-5), 115.22 (C-3), 70.51, 70.48, 68.93, 64.03 (12×OCH$_3$), 44.83 (CHCH$_3$), 18.35 (CHCH$_3$) ppm. 6b $^1$H NMR (CDCL$_3$) β 1.55 (d, 3H, CH$_3$), 3.10 (1H, OH), 3.54–3.74 (m, 22H, OCH$_2$), 3.81 (q, 1H, CHCH$_3$), 4.26 (m, 2H, COOCH$_2$), 7.12–7.55 (m, 8H, aromatic) ppm; $^{13}$C NMR (CDCL$_3$) β 173.66 (C=O), 159.40 (d, J=248 Hz, C-2), 141.57 (C-1), 135.21 (C-4), 130.51 (C-6), 128.67, 128.21, 127.42 (C-2', 3', 4'), 127.58 (C-1'), 123.38 (C-5), 115.06 (C-3), 72.36, 70.33, 70.27, 70.03, 68.74, 63.89, 61.39 (12×CH$_2$), 44.65 (CHCH$_3$), 18.18 (CHCH$_3$) ppm.

Synthesis of prodrugs from Triamcinolone Acetonide and Polyethylene Glycols (PEG). HO(CH$_2$CH$_2$O)nH, n=2, 3, 4

Polyethylene glycols have been linked via a carbonate bond to triamcinolone acetonide as shown in Scheme 3 below. The following procedure utilized the chloroformate of triamcinolone acetonide as an intermediate.

Triamcinolone acetonide (1 mmol) was dissolved in 15 mL of anhydrous dioxane and 5 mL of anhydrous tetrahydrofuran in a closed vial. The stirred mixture was cooled in an ice bath and anhydrous pyridine (80.9 μL) was added, then phosgene (8 mL of a 1.93M solution in toluene) was slowly added via a syringe. The vial was closed and the mixture was stirred at room temperature overnight. The progress of the reaction was monitored by TLC, using benzene:acetone (4:1) as a solvent system. After 16b the reaction was complete and the solvents were evaporated under vacuum on a rotary evaporator. The crude and unstable chloroformate of triamcinolone acetonide was dissolved in 15 mL of anhydrous dioxane and 5 mL of anhydrous tetrahydrofuran, and to this mixture 80.9 μL of anhydrous pyridine was added, followed by the appropriate polyethylene glycol (1 mmol). The mixture was stirred at room temperature overnight, concentrated on a rotary evaporator under vacuum and the residue redissolved in CH$_2$Cl$_2$ (30 mL). The solution was washed with water, brine and finally dried over anhydrous Na$_2$SO$_4$ and evaporated to afford a solid foam.

(a) Compound 8a.

The crude reaction residue (512 mg) was purified by chromatography. The column bed was washed with benzene:acetone (6:1) up to benzene:acetone (2:1), yielding 131.4 mg (23.2%) of the pure carbonate linked ester of triamcinolone acetonide and diethylene glycol 3a. $^1$H NMR (CDCx$_3$) β 0.94 (s, 3H, C-18), 1.21 (s, 3H, C-19), 1.41, 1.55 (2s, 6H, isopropylidene), 3.05 (m, 1H, OH), 3.40 (m, 1H, C-16), 3.58–3.85 (m, 6H, OCH$_2$), 4.30–4.40 (m, 2H, COOCH$_2$), 4.41–4.46 (m, 1H, C-11), 4.82, 5.05 (2d, 2H, C-21), 5.01 (d, 1H, OH), 6.15 (s, 1H, C-4), 6.36 (d, 1H, C-2), 7.32 (d, 1H, C-1) ppm; $^{13}$C NMR (CDCL$_3$) β 203.51 (C=O,C-20), 186.67 (C=O, C-3), 166.43 (C-5), 155.05 (OCOO), 152.55 (C-1), 129.54 (C-2), 124.91 (C-4), 111.52 (C, isopropylidene), 100.15 (d, C-9), 97.44 (C-17), 81.80 (C-16), 71.62 (C-11), 72.31 (C-21), 70.33, 68.90, 67.38, 61.60 (4×OCH$_2$), 48.19 (d, C-10), 45.58 (C-13), 42.97 (C-14), 36.71 (C-15), 33.59 (C-12), 33.15 (d, C-8), 30.84 (C-6), 27.51 (C-7), 26.40, 25.68 (2×CH$_3$, isopropylidene), 22.87 (d, C-19), 16.21 (C-18) ppm.

Compound 8b; Triamcinolone acetonide

The crude product (542 mg) was chromatographed with benzene:acetone (3:1) up to benzene:acetone (2:1) to yield 138.4 mg (22.7%) of the carbonate linked ester of triamcinolone acetonide and trimethylene glycol 8b as a white solid. $^1$H NMR (CDCL$_3$) β 0.94 (s, 3H, C-18), 1.21 (s, 3H, C-19), 1.42, 1.55 (2s, 6H, isopropylidene), 3.05 (m, 1H, OH), 3.47 (m, 1H, C-16), 3.58–3.80 (m, 10H, OCH$_2$), 4.25–4.34 (m, 1H, C-11), 4.36–4.51 (m, 2H, COOCH$_2$), 4.84, 5.01 (2d, 2H, C-21), 5.02 (d, 1H, OH), 6.13 (s, 1H, C-4), 6.34 (d,1H, C-2), 7.28 (d, 1H, C-1) ppm; $^{13}$C NMR (CDCL$_3$) β 203.41 (C=O, C-20), 186.57 (C=O, C-3), 166.24 (C-5), 154.90 (OCOO), 152.40 (C-1), 129.60 (C-2), 125.02 (C-4), 111.50 (C, isopropylidene), 99.64 (d, C-9), 97.41 (C-17), 81.77 (C-16, 71.71 (d, C-11), 72.20 (C-21), 70.61, 70.33, 70.22, 68.89, 67.39, 61.59 (6×OCH$_2$), 48.20 (d, C-10), 45.52 (C-13), 43.02 (C-14), 36.63 (C-15), 33.60 (C-12), 33.26 (d, C-8), 30.86 (C-6), 27.52 (C-7), 26.40, 25.64 (2×CH$_3$, isopropylidene), 22.88 (d, C-19), 16.17 (C-18) ppm.

Compound 8c; Triamcinolone acetonide

The yellow solid product (547 mg) was purified by chromatography. The column bed was washed with benzene:acetone (2:1) yielding 190 mg (29%) of the pure carbonate linked ester of triamcinolone acetonide and tetraethylene glycol 8c. $^1$H NMR (CDCL$_3$) β 0.95 (s, 3H, C-18), 1.20 (s, 3H, C-19), 1.42, 1.56 (2s, 6H, isopropylidene), 3.25 (s, 1H, OH), 3.40–3.55 (m, 1H, C-16), 3.60–3.85 (m, 14H, OCH$_2$), 4.28–4.35 (m, 1H, C-11), 4.35–4.50 (m,2H, COOCH$_2$), 4.92 (s, 2H, C-21), 5.01 (d, 1H, OH), 6.16 (s, C-4), 6.37 (d, 1H, C-2), 7.25 (d, 1H, C-1) ppm; $^{13}$C NMR (CDCL$_3$) β 203.63 (C=O, C-20), 186.42 (C=O, C-3), 165.79 (C-5), 155.03 (OCOO), 152.01 (C-1), 129.79 (C-2), 125.17 (C-4), 111.54 (C, isopropylidene), 100.09 (d, C-9), 97.53 (C-17), 81.89 (C-16), 71.76 (d, C-11), 72.54, 70.66, 70.61, 70.35, 70.22, 68.96, 67.81, 61.17 (8×OXH$_2$), 48.15 (d, C-10), 45.66 (C-13), 43.04 (C-14), 36.81 (C-15), 33.69 (C-12), 33.23 (d, C-8), 30.87 (C-6), 27.55 (C-7), 26.46, 25.73 (2×CH$_3$ isopropylidene), 22.97 (d, C-19), 16.30 (C-18) ppm.

Reaction of triamcinolone acetonide with the chloroformate of monoprotected tetraethylene glycol (Scheme 3 below).

To a solution of mono(t-butyldiphenylsilyl)tetraethylene glycol chloroformate (1 mmol) in 10 mL of a mixture of dry acetonitrile:dioxane:tetrahydrofuran (1:1:1) at 0° C. was added 113 μL of anhydrous pyridine and 1 mmol of triamcinolone acetonide. The resulting mixture was stirred at room temperature overnight, then evaporated to dryness, dissolved in dichloromethane and washed successively with water, brine, and finally dried over Na$_2$SO$_4$. The crude product was purified by chromatography (benzene:acetone, 9:1) to yield 402.5 mg (41%) of pure 9. $^1$H NMR (CDCl$_3$)δ 0.92 (s, 3H, C-18), 1.02 (s, 9H, t-Bu), 1.18 (s, 3H, C-19), 1.40, 1.54 (2s, 6H, isopropylidene), 3.55–3.60 (m, 1H, C-16), 3.60–3.75 (m, 12H, OCH$_2$), 3.75–3.82 (m, 2H, CH$_2$OSi), 4.25–4.35 (m, 2H, C-11), 4.79, 4.98 (2d, 2H, C-21), 6.10 (s, 1H, C-4), 6.32 (d, 1H, C-2), 7.15 (d, 1H, C-1), 7.30–7.70 (m, 6H, aromatic) ppm.

Deprotection of Compound 9.

To a solution of 402.5 mg of 9 in THF (8 mL) was added at 0° C. glacial acetic acid (134 μL) and a 1M solution of tetrabutylammonium fluoride in THF (1.2 mL). The reaction mixture was stirred at room temperature overnight, then evaporated to dryness, redissolved in ethyl acetate (20 mL) and washed successively with ammonium chloride solution, water and brine. Drying over Na$_2$SO$_4$ and solvent evaporation left a yellow solid product, which was purified by column chromatography (benzene:acetone, 2:1). The triamcinolone-tetraethylene glycol prodrug 8c was obtained as a white powder (191 mg, 64.7% yield).

Synthesis of prodrugs from 5β-pregnane-3α,17α,21-triol-20-one (THS) and polyethylene glycols (PEG), HO(CH$_2$CH$_2$O)H n=2, 4.

Polyethylene glycols have been linked to THS via a carbonate moiety as shown in Scheme 4 below. This approach requires the selective protection of one of the two hydroxyl groups of the PEG as a silyl derivative and allows one to obtain and easily separate three protected prodrugs in one reaction. Subsequent separation and deprotection of the above mixture of products led to the expected prodrugs: the C-3α, C-21 bicarbonate ester of THS with the appropriate PEG, the C-3α monocarbonate ester of THS with the appropriate PEG, the C-21 monocarbonate ester of THS and the appropriate PEG. The following example describes the classical procedure for the preparation of these prodrugs.

An appropriate mono(t-butyldiphenylsilyl)polyethylene glycol (2 mmol) was dissolved in 18 mL of anhydrous tetrahydrofuran. The stirred solution was cooled in an ice bath and anhydrous pyridine (161.8 μL) was added and then phosgene (16 mL of a 1.93M solution in toluene) was slowly added via a syringe. The vial was closed and the mixture was stirred overnight at room temperature. The progress of the reaction was monitored by TLC using hexane:ethyl acetate (9:1) as a solvent system. After 18 hours the reaction was completed and the solvents were evaporated under vacuum on a rotary evaporator. The crude and unstable chloroformate was redissolved in an acetonitrile: tetrahydrofuran (1:1) mixture (20 mL) and to this solution 162 μL of anhydrous pyridine was added, followed by the trishydroxysteroid (1 mmol). The mixture was stirred overnight at room temperature, concentrated on a rotary evaporator and redissolved in ethyl acetate (80 mL). The solution was washed with water, brine, dried over anhydrous Na$_2$SO$_4$, evaporated to an oil and the reaction products separated: Compounds 10, 11 and 12

The crude oil (995 mg) was separated by chromatography. The column bed was washed with benzene:acetone (40:) up to benzene:acetone (4:1), to give three fractions. The first fraction contained the less polar C-3α, C-21-bicarbonate ester of THS and monoprotected diethylene glycol 10 (403.6 mg, 37%), the second fraction contained the more polar C-3α-carbonate ester of THS and monoprotected diethylene glycol 11 (106.5 mg, 14.8%), the third fraction contained the most polar C-21 carbonate ester of THS and monoprotected diethylene glycol 12 (166.2 mg, 23.1%), all compounds were obtained as white solid foams. 10 $^1$H NMR (CDCl$_3$) δ 0.68 (s, 3H, C-18), 0.96 (s, 3H, C-19), 1.1 (s, 18H, t-Bu), 2.35 (s, 1H, C-17αOH), 3.6–3.8 (m, 8H, OCH$_2$), 3.8–3.9 (m, 4H, CH$_2$OSi), 4.23–4.38 (m, 4H, OCOOCH$_2$), 4.57–4.69 (m, 1H, C-3), 4.87, 5.17 (2d, 2H, C-21), 7.37–7.79 (m, 20H, aromatic) ppm. 11 $^1$H NMR (CDCl$_3$) δ 0.63 (s, 1H, C-18), 0.93 (s, 3H, C-19), 1.05 (s, 9H, t-Bu), 2.2 (s, 1H, C-17αO H), 2.30–2.45 (m, 1'H, C-21-OH), 3.55–3.78 (m, 4H, OCH$_2$), 3.80–3.84 (m, 2H, CH$_2$OSi), 4.19–4.28 (m, 2H, OCOOCH$_2$), 4.25, 4.67 (2d, 2H, C-21), 4.52–4.61 (m, 1H, C-3), 7.35–7.73 (m, 10H, aromatic) ppm. 12 $^1$H NMR (CDCl$_3$) δ 0.63 (s, 3H, C-18), 0.96 (s, 3H, C-19), 1.04 (s, 9H, t-Bu), 2.08 (s, 1H, C-17-OH), 2.95 (s, 1H, C-3αOH), 3.55–3.65, 3.70–3.87 (m, 4H, OCH$_2$), 3.65–3.70 (m, 1H, C-3), 3.88–4.05 (m, 2H, CH$_2$OSi), 4.25–4.35 (m, 2H, OCOOCH$_2$), 4.81, 5.15 (2d, 2H, C-21), 7.32–7.72 (m, 10H, aromatic) ppm.

Compounds 13, 14 and 15; THS

The oily residue (911 mg) was separated by chromatography. The column was washed with benzene:acetone (15:1) up to benzene:acetone (6:1). Three fractions were collected: the first fraction contained the less polar C-3α,C-21-bicarbonate ester of THS and monoprotected tetraethylene glycol 13 (202.2 mg, 16.2% yield), the second fraction contained the C-3α-monocarbonate ester of THS and monoprotected tetraethylene glycol 14 (228.6 mg, 28.1% yield) and finally the third fraction contained the C-tetraethylene glycol 14 (228.6 mg, 28.1% yield) and finally the third fraction contained the C-tetraethylene glycol 14 (228.6 mg, 28.1% yield) and finally the third fraction contained the C-21-carbonate ester of THS and monoprotected tetraethylene glycol 15 (222 mg, 27.4%), all compounds were obtain as colorless oils. 13 $^1$H NMR (CDCL$_3$) β 0.62 (s, 3H, C-19), 0.93 (s, 3H,C-19), 1.02 (s, 18H, t-Bu), 2.01 (s, 1H, C-17αO H), 3.55–3.76 (m, 24H, OCH$_2$), 3.78–4.02 (m, 4H, CH$_2$OSi), 4.22–4.34 (m, 4H, OCOOCH$_2$), 4.50–4.65 (m, 1H, C-3), 4.82, 5.13 (d, 2H, C-21),7.35–7.74 (m, 20H, aromatic) ppm. 14 $^1$H NMR (CDCL$_3$) β 0.61 (s, 3H, C-8), 0.93 (s, 3H, C-19), 1.02 (s, 9H, t-Bu), 2.08 (s, 1H, C-17αO H), 3.09 (t, 1H, C-21-OH), 3.58–3.75 (m, 12H,OCH$_2$), 3.77–4.83 (m, 2H, CH$_2$OSi), 4.23–4.26 (m, 2H, OCOOCH$_2$), 4.30, 4.68 (2d, 2H, C-21), 4.5–4.65 (m, 1H, C-3), 7.35–7.72 (m, 10H, aromatic) ppm. 15 $^1$H, aromatic) ppm. 15 $^1$H NMR (CDCL$_3$) β 0.63 (s, 3H, C-18), 0.92 (s, 3H, C-19), 1.02 (s, 9H, t-Bu), 2.21 (s, 1H, C-17αOH), 3.55–3.58 (m, 2H, CH-3α-OH), 3.60–3.78 (m, 12H, OCH$_2$), 3.79–4.03 (m, 2H, CH$_2$), 3.79–4.03 (m, 2H, CH$_2$OSi), 4.27–4.35 (m, 2H, OCOOCH$_2$), 4.82–5.14 (2×d, 2H, C-21 ), 7.34–7.74 (m, 10H aromatic) ppm.

Deprotection of THS-PEG (n=2)-silyl Derivatives (Scheme 4 below)

Deprotection of Compound 10

A 1M solution of tetrabutylammonium fluoride in THF (2 mL) was added to an ice-cold solution of 10 (403.6 mg, 0.37 mmol) in glacial acetic acid (222 μL) and tetrahydrofuran (15 mL). The mixture was stirred overnight at room temperature, concentrated, redissolved in ethyl acetate and washed with ammonium chloride solution, water, brine and finally dried over Na$_2$SO$_4$. The product was purified by column chromatography (benzene:acetone, 6:1 up to benzene:acetone, 4:1) yielding 175 mg (77%) of the C-3α, C-21 bicarbonate ester of THS and diethylene glycol, 16, as a white stable foam. $^1$H NMR (CDCL$_3$) β 0.63 (s, 3H, C-18), 0.96 (s, 3H, C-19), 2.78–2.88 and 3.01–3.13 (2m, 2H, CH$_2$O H), 3.28 (s, 1H, C-17αOH), 3.62–3.81 (m, 12H, OCH$_2$), 4.25–4.28 (m, 2H, C-3α-OCOOCH$_2$), 4.29–4.38 (m, 2H, C-21-OCOOCH$_2$), 4.51–4.65 (m, 1H, C-3), 4.85, 5.17 (2d, 2H, C-21) ppm; $^{13}$C NMR (CDCL$_3$) β 205.54 (C=O, C-20), 154.80 (C-21-OCOO), 154.40 (C-3αOCOO), 89.82 (C-17), 78.23 (C-3αOCOO), 72.40 (C-21-OCOOCH$_2$), 72.27 (C-3αOCOOCH$_2$, 70.71 (C-21-OCOO), 68.73 (C-3αOCOOCH$_2$CH$_2$), 68.75 (C-21-OCOOCH$_2$CH$_2$), 67.10 (C-21-OCOOCH$_2$CH$_2$OCH$_2$CH$_2$OH), 66.41 (C-3αOCOOCH$_2$CH$_2$OCH$_2$CH$_2$OH), 61.43 2×CH$_2$CH$_2$OH), 50.90 (C-14), 48.36 (C-13, 41.57 (C-5), 39.80 (C-9), 35.63 (C-8), 34.72 (C-2), 34.54 (C-1), 34.37 (C-10), 31.87 (C-4), 30.33, 26.28 (C-16,C-12), 26.27 (C-6, C-7), 23.48 (C-15), 23.03 (C-19), 20.32 (C-11), 14.37 (C-18) ppm.

Deprotection of Compound 11.

To a solution of 106.5 mg of 11 in tetrahydrofuran (10 mL) at 0° C. was added glacial acetic acid (44 µL) and a 1M solution of tetrabutylammonium fluoride in THF (395 µL). The reaction mixture was stirred at room temperature overnight and after typical work-up, and separation by chromatography (benzene:acetone, 9:1 up to benzene:acetone, 6:1) was obtained 55.2 mg (77.4% yield) of the C-3α monocarbonate ester of THS and diethylene glycol, 17, as a white solid foam. $^1$H NMR (CDCL$_3$) β 0.62 (s, 3H, C-18), 0.95 (s, 3H, C-19), 2.37–2.45 (m, 1H, CH$_2$CH$_2$OH), 2.55 (s, 1H, C-17αOH), 3.18 (t, 1H, C-21-OH),3.57–3.78 (m, CH, OCH$_2$), 4.23–4.35 (m, 2H, C-3αOCOOCH$_2$), 4.30, 4.68 (2×d, 2H, C-21), 4.54–4.60 (m, 1H, CH-CαOOO) ppm; $^{13}$C NMR (CDCL$_3$) β214.43 (C=O, C-20), 154.60 (C-3αO COO), 89.22 (C-17), 78.30 (C-3αOCOO), 72.31 (C-3αOCOOCH$_2$), 68.91 (C-3α-OCOOCH$_2$CH$_2$) 67.38 (C-21-OH), 66.51 (C-3αOCOOCH$_2$CH$_2$OCH$_2$CH$_2$OH), 61.65 (2×CH$_2$CH$_2$OH), 50.91 (C-14), 48.83 (C-13), 41.69 (C-5), 40.03 (C-9), 35.7 (C-8), 34.85(C-2), 34.58 (C-1), 34.50 (C-10), 31.98 (C-4), 30.47, 26.79 (C-16, C-12), 26.40 (C-6, C-7), 23.72 (C-15), 23.12 (C-19), 20.29 (C-11, 15.06 (C-18) ppm.

Deprotection of Compound 12

To a solution of 166.2 mg of 12 in THF (12 mL) at 0° C. was added glacial acetic acid (68 µL), followed by a 1M solution of tetrabutylammonium fluoride in THF (61 mL). After overnight stirring at room temperature and classical work-up with final separation by chromatography (benzene:acetone, 4:1 up to benzene:acetone, 2:1) was obtained 95.1 mg (83.9% yield) of the C-21 monocarbonate ester of THS and diethylene glycol, 18, as a white solid foam. $^1$H NMR (CDCL$_3$) β 0.61 (s, 3H, C-18), 0.90 (s, 3H, C-19), 2.48 (s, 1H, C-17αOH), 2.95–3.10 (m, 1H, CH$_2$CH$_2$OH), 3.46 (s, 1H, C-3αOH), 3.53–3.80 (m, 7H, OCH$_2$ and CH-3αOH), 4.27–4.42 (m, 2H, C-21-OCOOC H$_2$), 4.82, 5.18 (2×d, 2H, C-21) ppm. $^{13}$C NMR (CDCL$_3$) β 205.72 (C=O), 154.91 (C-21-OCOO), 89.93 (C-17), 72.49 (C-21-OCOOCH$_2$), 71.60 (C-3αOH), 70.84 ( C-21-OCOO), 68.73 (C-21-OCOOCH$_2$CH$_2$), 67.19 (C-21-OCOOCH$_2$OCH$_2$CH$_2$CGH$_2$OH), 61.51 (CH$_2$CH$_2$OH), 51.05 (C-14), 48.48 (C-13), 41.87 (C-5), 39.96 (C-9), 35.78 (C-8), 36.03 (C-2), 35.23 (C-1), 34.55 (C-10), 30.46 (C-4), 30.44, 30.31 (C-16, C-12), 26.97, 26.49 (C-6, C-7), 23.56 (C-15), 23.20 (C-19, 20.39 (C-11), 14.48 (C-18) ppm.

Deprotection of THS-PEG(n=4)-Silyl Derivatives (Scheme 4 below)

Deprotection of Compound 13

To a solution of 202 mg of 13 in THF (15 mL) at 0° C. was added glacial acetic acid (92 µL) and then a 1M solution of tetrabutylammonium fluoride in THF (870 µL). After overnight reaction at room temperature, extraction, as described above, and separation by column chromatography with benzene:acetone (1:1), the C-3α, C-21 bicarbonate ester of THS and tetraethylene glycol 19 (103.8 mg, 82% yield), was obtained as a colorless oil. $^1$H NMR (CDCL$_3$) β 0.68 (s, 3H, C-18, 0.95 (s, 3H, C-19), 2.53 (s, 1H, C-17αO H), 2.55 (m, 2H, CH$_2$CH$_2$OH), 3.58–3.82 (m, 28H, OCH$_2$), 4.23–4.30 (m, 2H, C-3αOCOOCH$_2$), 4.30–4.37 (m, 2H, C-21-OCOOCH$_2$), 4.52–4.63 (m, 1H, CH-3αOCOO), 5.01, 5.18 (2d, 2H, C-21) ppm; $^{13}$C NMR (CDCL$_3$) β 204.73 (C=O, C-20, 154.82 (C-21-OCOO), 154.50 (C-3αO COO), 90.13 (C-17), 78.10 (C-3αOCOO), 72.46 (C-21-OCOOCH$_2$), 72.44 (C-3αOCOOCH$_2$), 70.66 (C-21=OCOO), 70.64, 70.56, 70.50, 70.39, 70.35, 70.31, 68.94, 68.92 (10×OCH$_2$), 67.43 (C-21-OCOO-PEG-O CH$_2$CH$_2$OH), 66.62 (C-3αOCOO-PEG-OCH$_2$CH$_2$OH), 61.74 (2×CH$_2$CH$_2$OH), 51.17 (C-14), 48.55 (C-13), 41.70 (C-5), 40.05 (C-9), 35.75 (C-8), 34.94 (C-2), 34.88 (C-1), 34.50 (C-10), 31.99 (C-4), 30.56, 26.80 (C-16, C-12), 26.40 (C-6, C-7), 23.59 (C-15), 23.12 (C-19, 20.41 (C-11), 14.65 (C-18 ppm.

Deprotection of Compound 14

To a solution of 228.6 mg of 14 in THF (15 mL) at 0° C. was added glacial acetic acid (75 µL) and then a 1M solution of tetrabutylammonium fluoride in THF (690 µL). According to the procedure in (a) above, by using benzene:acetone (2:1) for chromatographic separation, the C-3α-monocarbonate ester of THS and tetraethylene glycol 20 (112.8 mg, 79.8% yield), was obtained as a colorless oil. $^1$H NMR (CDCL$_3$) β 0.63 (s, 3H, C-18), 0.95 (s, 3H, C-19), 2.30 (s, 1H, C-17αOH), 2.53–2.60 (m, 1H, CH$_2$CH$_2$OH), 3.11 (t, 1H, C-21-OH), 3.62–3.81 (m, 14H, OCH$_2$), 4.23–4.30 (m, 2H, C-3αOCOOCH$_2$), 4.30, 4.68 (2×d, 2H, C-21), 4.52–4.62 (m, 1H, CH-3αOCOO) ppm; $^{13}$C NMR (CDCL$_3$) β 212.32 (C=O, C-20), 154.50 (C-3αOCOO), 89.27 (C-17), 78.12 (C-3αOCOO), 72.45 (C-3αOCOO CH$_2$), 70.62, 70.55, 70.48, 70.33, 68.94 (5×OCH$_2$), 67.41 (C-21-OH), 66.62 (CH$_2$CH$_2$OH), 61.74 (CH$_2$CH$_2$OH), 50.97 (C-14), 48.90 (C-13), 41.68 (C-5), 40.07 (C-9), 35.73 (C-8), 34.86 (C-2), 34.64 (C-1), 34.50 (C-10), 31.97 (C-4), 30.49, 26.77 (C-16, C-12), 26.39 (C-6, C-7), 23.72 (C-15), 23.11 (C-19), 20.28 (C-11), 15.10 (C-18) ppm.

Deprotection of Compound 15

Using the same molar ratio of glacial acetic acid to tetrabutylammonium fluoride as was described in procedure (b) above, 222 mg of 15 afforded the C-21-monocarbonate ester of THS and tetraethylene glycol 21 (113 mg, 80.2% yield), as a white solid foam. $^1$H NMR (CDCL$_3$) β 0.62 (s, 3H, C-18), 0.92 (s, 3H, C-19), 2.28 (s, 1H, C-17αOH), 2.80–2.90 (m, 1H, CH$_2$CH$_2$OH), 3.40 (s, 1H, CH-3αOH), 3.55–3.80 (m, 15H, OCH$_2$ and CH-3αOH), 4.25–4.40 (m, 2H, C-21-OCOOCH$_2$), 4.81, 5.17 (2×d, 2H, C-21) ppm; $^{13}$C NMR (CDCL$_3$) β 205.65 (C=O, C-20), 154.81 (C-21-O COO), 89.90 (C-17), 72.47 (C-21-OCOOCH$_2$), 71.58 (C-3αOH), 70.79 (C-21-OCOO), 70.58, 70.41, 70.40, 70.31, 68.85 (5×OCH$_2$), 67.20 (OCH$_2$CH$_2$OH), 61.52 (CH$_2$ CH$_2$OH), 51.02 (C-14), 48.30 (C-13), 41.50 (C-5), 40.20 (C-9), 36.01 (C-2), 35.76 (C-8) 34.25 (C-1), 34.48 (C-10), 34.45 (C-4), 30.40, 30.29 (C-16, C-12), 26.92 (C-6), 26.48 (C-7), 23.58 (C-15), 23.20 (C-19), 20.40 (C-11), 14.52 (C-18) ppm.

Synthesis Example of Prodrugs from Gancyclovir and diethylene glycol (Numbers refer to synthesis scheme where appropriate).

185 mg of N-protected gancyclovir (1) was dissolved in a mixture of dry acetonitrile (2 mL) and dry THF (2 mL) followed by addition of anhydrous pyridine (97 µL). The mixture was cooled in an ice-bath and a solution of 428 mg of the chloroformate (2) in 2 mL of THF was slowly added.

The resulting mixture was stirred at room temperature for 16 h, and the solvents were evaporated. The oily residue was redissolved in 10 mL of chloroform, washed with water (2×), brine and dried over sodium sulfate. The residue after solvent evaporation was chromatographed on silicagel. Elution with benzeneacetone yielded 200 mg of dicarbonate (3). The structure of this intermediate was confirmed by 1H and 13C NMR spectroscopy.

53 mg of (3) was dissolved in 1.5 mL of THF and 200 µL of commercial tetrabutyl ammonium fluoride in THF was added. The resulting solution was stirred at 40° C. overnight, evaporated to dryness and redissolved in 3 mL of 80% acetic acid. The mixture was heated at 50° C. for 4 h and evaporated under vacuum. The residue was purified by column chromatography on silicagel to give 14 mg of prodrug (4). $^1$H-NMR(300 MHz, CD$_3$OD) δ 3.45(m,4H), 3.58(m,8H), 4.00–4.20(m,9H), 5.45(s,2H), 7.75(s,1H), $^{13}$C-NMR(75.429 MHz, CD$_3$OD) δ 62.1, 67.5, 68.4, 69.8, 73.1, 73.6(6× CH$_2$O), 75.9(CHO), 117.6(C-5), 153.3(C-4), 155.6(C-2), 156.3(OCOO), 159.4(C-6)ppm.
Gancyclovir Synthesis Scheme 40 mg of DDI (dideoxyinosine) was suspended in 2 mL of dry acetonitrile and 60 mg of carbonyldiimidazole was added. The resulting suspension was stirred at room temperature for 3 h and to the resulting homogenous solution a monoprotected diethylene glycol (5) was added. The mixture was then stirred at 90° C. for 36 h. The residue obtained after solvent evaporation was chromatographed on silicagel

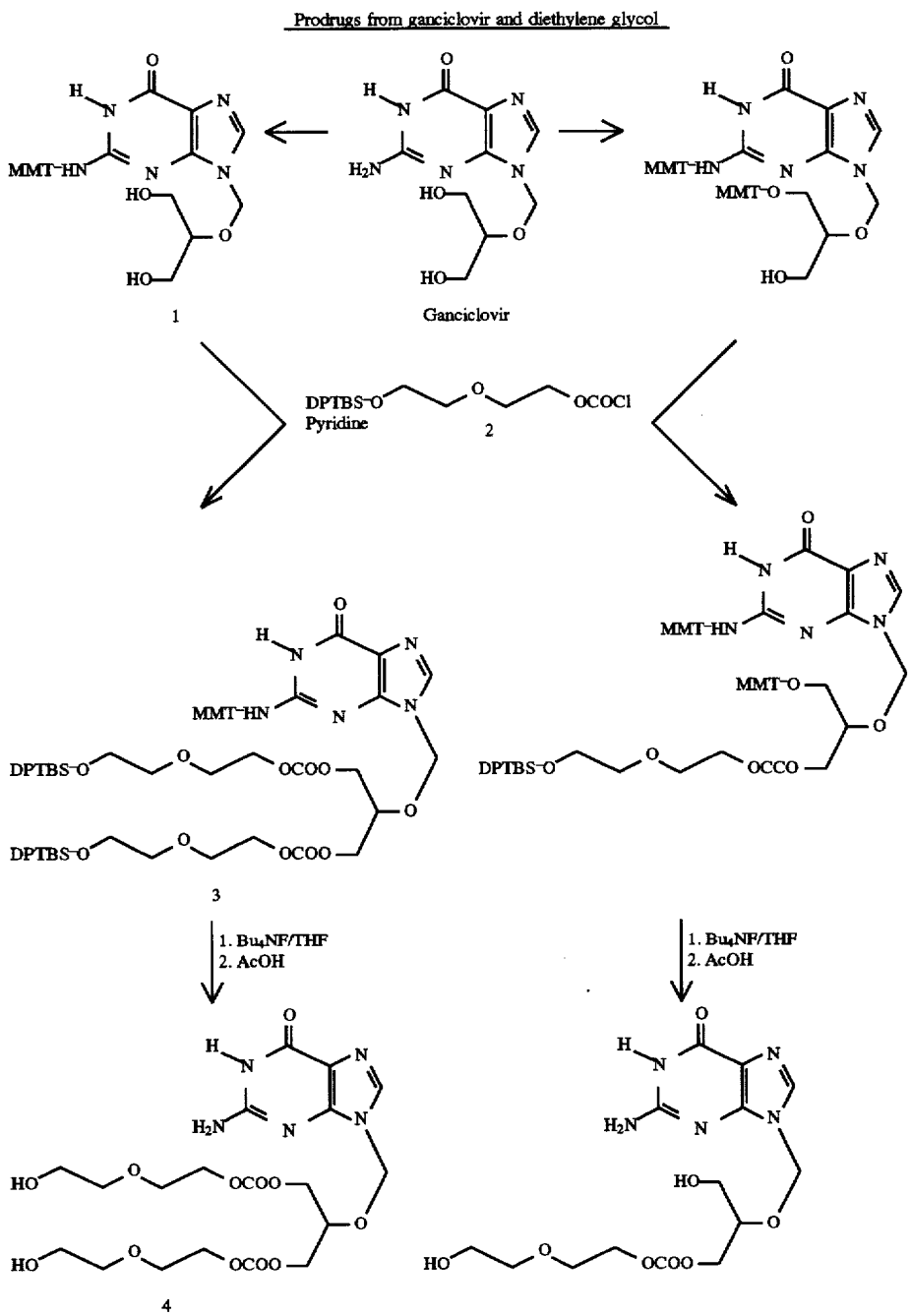

Synthesis Example of Prodrugs from DDI and diethylene glycol with chloroform-methanol solvent system to yield 45 mg of (6). The carbonate (6) was dissolved in 1 mL of THF and 150 μL of tetrabutylammonium fluoride solution was added followed by 150 μL of acetic acid. The reaction mixture was stirred at room temperature for 24 h, and the product was purified by preparative thin-layer chromatography to yield 12 mg of carbonate (7). $^1$H-NMR(300 MHz, CDCl$_3$) δ 2.20(m,2H), 2.55(m,2H), 3.65–4.5(m,13H), 6.30(t,1H), 8.18 (s,1H), 8.22(s,1H). $^{13}$C-NMR(75.429 MHz, CDCl$_3$) δ 25.8 (C-3'), 32.7(c-2'), 61.3, 67.4, 67.8, 68.6, 72.8 (5×CH$_2$O), 78.5(C-4'), 85.0(C-1'), 125.0(C-5), 146.6(C-2), 148.2(C-4), 155.0(OCOO), 158.3(C-6) ppm.
DDI Synthesis Scheme
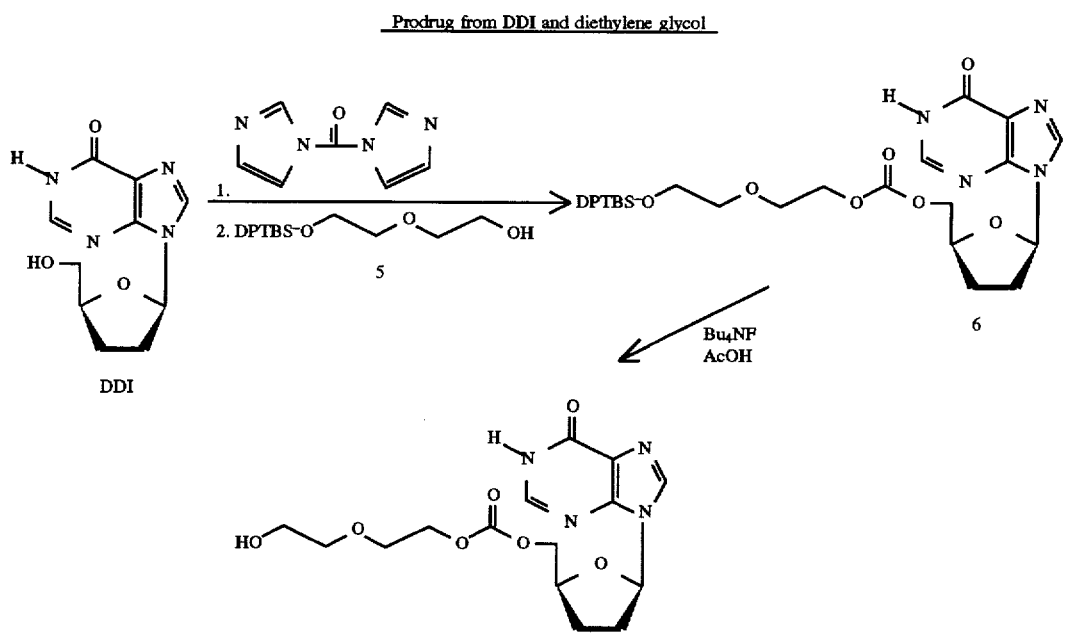
DPTBS = diphenyl-t-butylsilyl
SCHEME 1
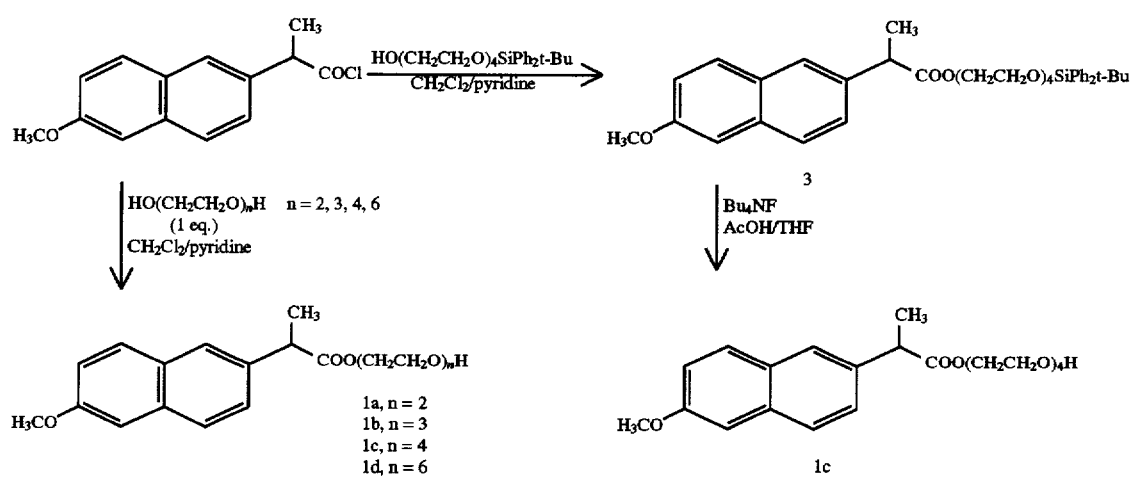

-continued
SCHEME 1
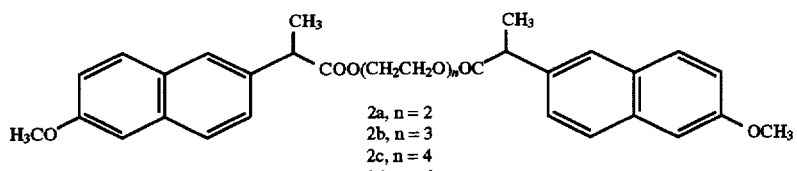
2a, n = 2
2b, n = 3
2c, n = 4
2d, n = 6
Naproxen + PEG
SCHEME 2
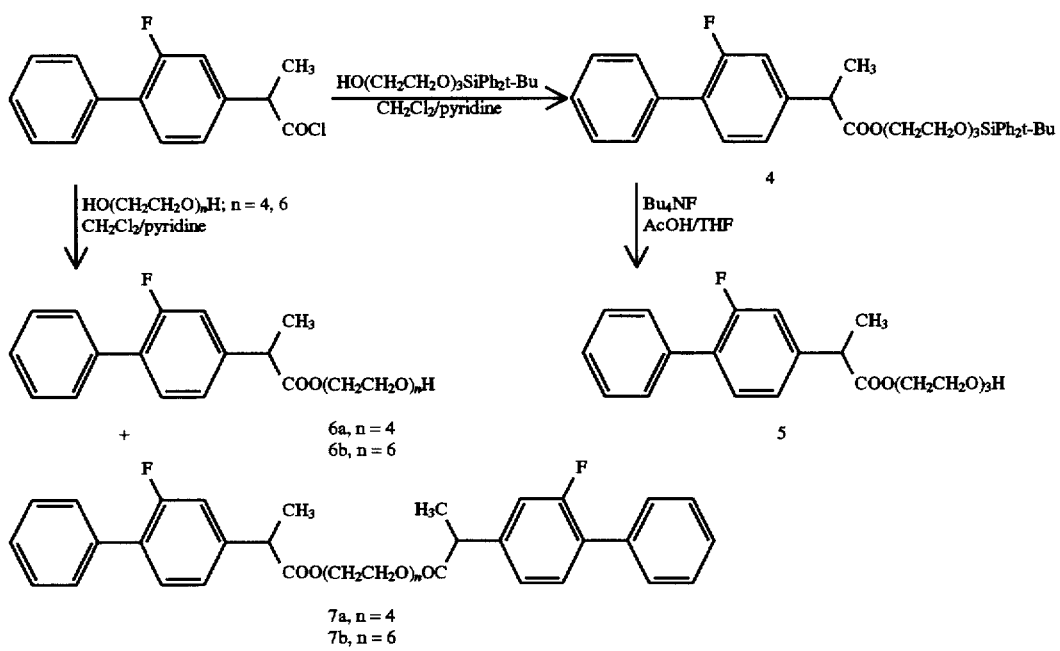
6a, n = 4
6b, n = 6
7a, n = 4
7b, n = 6
Flurbiprofen + PEG
SCHEME 3
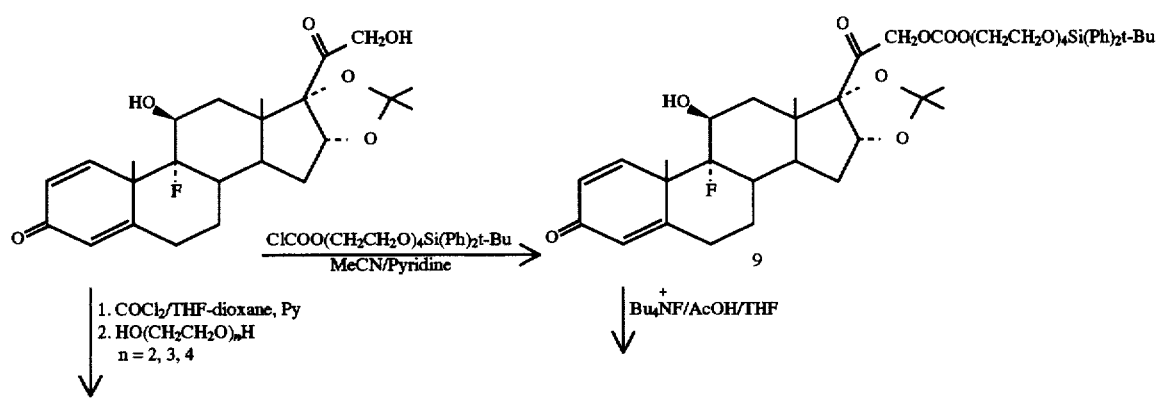

-continued
SCHEME 3

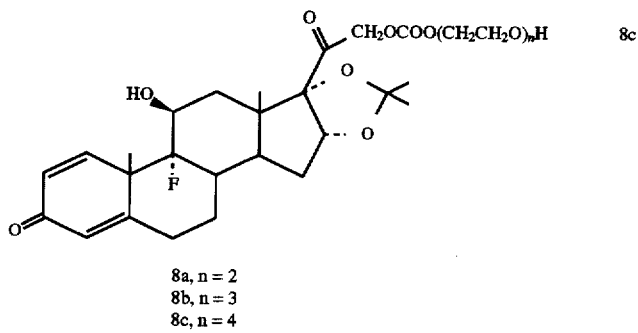

8a, n = 2
8b, n = 3
8c, n = 4

Triamcinolone Acetonide + PEG

SCHEME 4

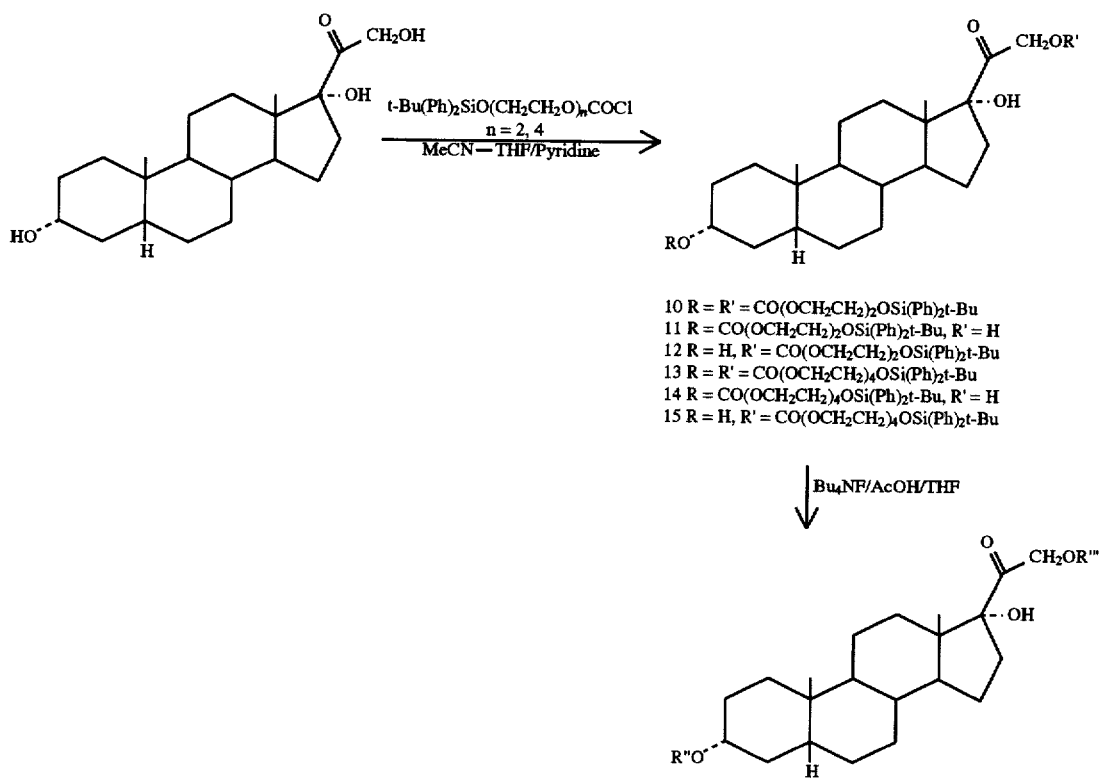

10 R = R' = CO(OCH$_2$CH$_2$)$_2$OSi(Ph)$_2$t-Bu
11 R = CO(OCH$_2$CH$_2$)$_2$OSi(Ph)$_2$t-Bu, R' = H
12 R = H, R' = CO(OCH$_2$CH$_2$)$_2$OSi(Ph)$_2$t-Bu
13 R = R' = CO(OCH$_2$CH$_2$)$_4$OSi(Ph)$_2$t-Bu
14 R = CO(OCH$_2$CH$_2$)$_4$OSi(Ph)$_2$t-Bu, R' = H
15 R = H, R' = CO(OCH$_2$CH$_2$)$_4$OSi(Ph)$_2$t-Bu

16 R" = R'" = CO(OCH$_2$CH$_2$)$_2$OH
17 R" = CO(OCH$_2$CH$_2$)$_2$OH, R'" = H
18 R" = H, R'" = CO(OCH$_2$CH$_2$)$_2$OH
19 R" = R'" = CO(OCH$_2$CH$_2$)$_4$OH
20 R" = CO(OCH$_2$CH$_2$)$_4$OH, R'" = H
21 R" = H, R'" = CO(OCH$_2$CH$_2$)$_4$OH

Trishydroxysteroid + PEG

Table 1 below shows examples of the half-life and solubility several of the compounds of the invention.

TABLE 1

| Number | Compound | t½ in serum | t½ in PB (7.4) | Solubility |
|---|---|---|---|---|
| G-195.1 | NPX-diEG | 58 mins | 80 hrs | 0.553 ± 0.027 mg/ml |
| G-192.1 | NPX-triEG | 13 mins | 230 hrs | 0.943 ± 0.025 mg/ml |
| G-167 | NPX-tetraEG | 5 mins | 300 hrs | 1.115 ± 0.031 mg/ml |
| G-220.1 | NPX-hexEG | 3.7 mins | several days | 6.433 ± 0.617 mg/ml |
| G-195.2 | NPX-diEG-NPX | 75 mins | low solubility | <0.1 ug/ml |
| G-192.2 | NPX-triEG-NPX | 50 mins | low solubility | <0.1 ug/ml |
| G-219.2 | NPX-tetraEG-NPX | 26 mins | very slow | <0.1 ug/ml |
| G-220.2 | NPX-hexEG-NPX | 50 mins | very slow | <0.1 ug/ml |
| G-60 | FB-triEG | 45 mins | 175 hrs | 0.135 ± 0.004 mg/ml |
| G-202.1 | FB-tetraEG | 32 mins (curve) | 144 hrs | 0.228 ± 0.005 mg/ml |
| TC-242.2 | FB-hexEG | 22 mins | several days | 0.445 ± 0.034 mg/ml |
| G-202.2 | FB-tetraEG-FB | 220 mins | low solubility | <0.1 ug/ml |
| TC-242.1 | EB-hexEG-FB | 167 mins | very slow | <0.1 ug/ml |
| G-197.1 | Triam-diEG | 10 mins | 101 hrs | 0.074 ± 0.003 mg/ml |
| G-201.1 | Triam-triEG | 88 mins | 120 hrs | 0.288 ± 0.006 mg/ml |
| G-196.1 | Triam-tetraEG | 228 mins | 136 hrs | 0.391 ± 0.049 mg/ml |

Thus, the above disclosure relates to non-steroidal or steroidal anti-inflammatory prodrugs and a method of use thereof. Soluble ester prodrugs of polyethylene glycol (PEG) and naproxen, triamcinolone acetonide, taxol, DDI, cyclosporin, gancyclovir or trihydroxy steroid prodrugs, and flurbiprofen prodrugs, etc., are described and a method of using these esters for relieving inflammation or other disease condition or symptom as appropriate. Methods of making and using the prodrugs of the invention are described above.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation. All patents or publications cited herein are incorporated by reference in their entireties.

We claim:

1. A polyethylene glycol ester prodrug comprising a compound selected from the group consisting of a steroidal compound, an antiviral compound, an immunomodulating compound, an anti-tumor compound, a neovascular compound, and a non-steroidal compound, which non-steroidal compound is selected from the group consisting of indomethacin, dideoxyinosine (DDI) and gancyclovir, with said compound linked via an ester linkage to a polyethylene glycol having the formula $HO(CH_2CH_2O)_nH$, wherein n=2–12.

2. A pharmaceutical composition comprising a prodrug according to claim 1 and a carrier.

3. A prodrug according to claim 1 wherein said steroidal compound is selected from the group consisting of triamcinolone acetonide and trihydroxysteroid.

4. A prodrug according to claim 1 wherein n=2–6.

5. A prodrug according to claim 1 wherein n=3–6.

6. A prodrug according to claim 1 wherein said steroidal or non-steroidal compound is linked to said polyethylene glycol by a carbonate group.

7. A prodrug according to claim 1, selected from the following compound formulas:

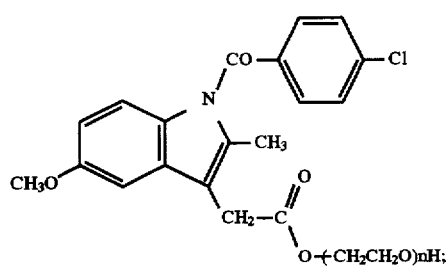

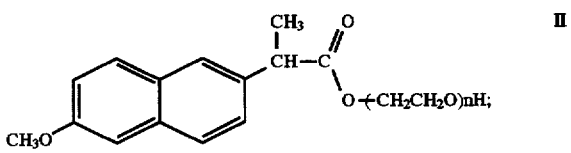

-continued

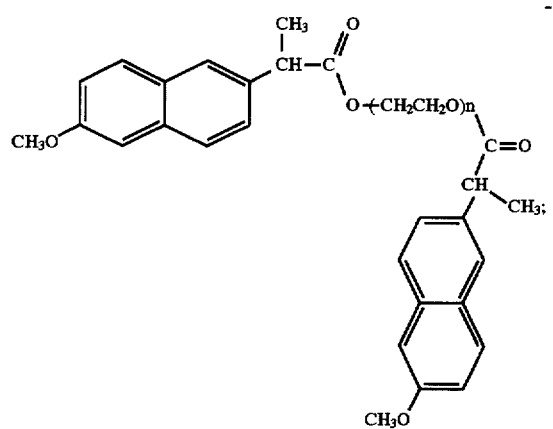

III

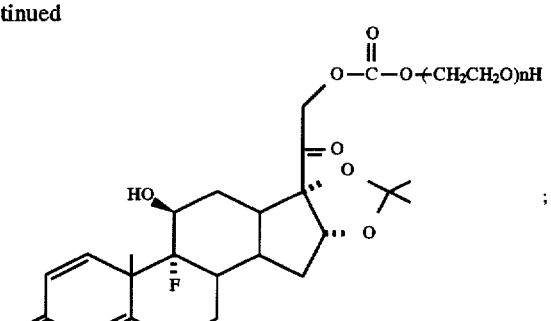

IV

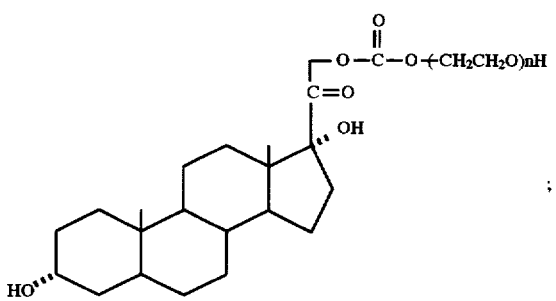

V

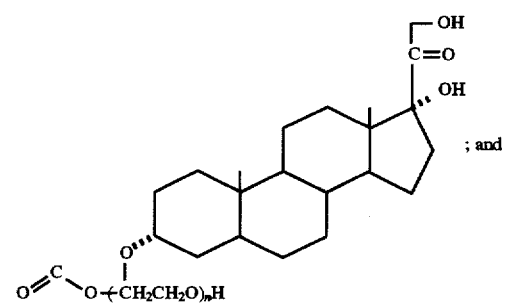

VI

; and

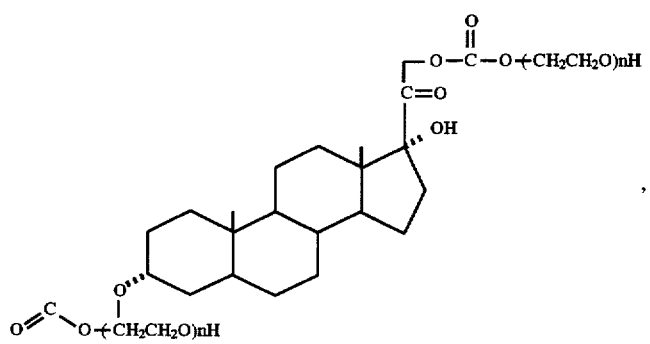

VII

, wherein n = 2–12.

8. A prodrug according to claim 1 wherein said immunomodulating compound is cyclosporin.

9. A prodrug according to claim 1 wherein said anti-tumor compound is taxol.

10. A method of treating a human or animal having a disease condition or symptom comprising administering an effective amount of a prodrug according to claim 1 to said human or animal having such disease condition or symptom.

* * * * *